United States Patent [19]

Mann et al.

[11] Patent Number: 4,788,980
[45] Date of Patent: Dec. 6, 1988

[54] PACEMAKER HAVING PVC RESPONSE AND PMT TERMINATING FEATURES

[75] Inventors: Brian M. Mann; Stuart W. Buchanan, both of Los Angeles, Calif.

[73] Assignee: Siemens-Pacesetter, Inc., Sylmar, Calif.

[21] Appl. No.: 887,297

[22] Filed: Jul. 18, 1986

[51] Int. Cl.[4] .............................................. A61N 1/36
[52] U.S. Cl. .............................................. 128/419 PG
[58] Field of Search .................................. 128/419 PG

[56] References Cited

U.S. PATENT DOCUMENTS

| | | | |
|---|---|---|---|
| 4,023,121 | 5/1977 | Alley, III | 128/419 PG |
| 4,307,725 | 12/1981 | Sowton et al. | 128/419 PG |
| 4,343,311 | 8/1982 | Markowitz | 128/419 PG |
| 4,408,606 | 10/1983 | Spurrell et al. | 128/419 PG |
| 4,421,116 | 12/1983 | Markowitz | 128/419 PG |
| 4,488,553 | 12/1984 | Nappholz et al. | 128/419 PG |
| 4,488,554 | 12/1984 | Nappholz et al. | 128/419 PG |
| 4,505,276 | 3/1985 | Markowitz et al. | 128/697 |
| 4,523,593 | 6/1985 | Rueter | 128/419 PG |
| 4,539,991 | 9/1985 | Boute et al. | 128/419 PG |
| 4,541,430 | 9/1985 | Elmqvist et al. | 128/419 PG |
| 4,548,209 | 10/1985 | Wielders et al. | 128/419 D |
| 4,554,920 | 11/1985 | Baker, Jr. et al. | 128/419 PG |
| 4,554,921 | 11/1985 | Boute et al. | 128/419 PG |
| 4,559,946 | 12/1985 | Mower | 128/419 D |
| 4,569,350 | 2/1986 | Mumford et al. | 128/697 |
| 4,572,192 | 2/1986 | Jackman et al. | 128/419 PG |
| 4,577,633 | 3/1986 | Berkovits et al. | 128/419 PG |
| 4,577,634 | 3/1986 | Gessman | 128/419 PG |
| 4,587,970 | 5/1986 | Holley | 128/419 PG |
| 4,593,695 | 6/1986 | Wittkampf | 128/419 PG |
| 4,644,954 | 2/1987 | Wittkampf et al. | 128/419 PG |
| 4,686,989 | 8/1987 | Smyth et al. | 128/419 PG |
| 4,712,556 | 12/1987 | Baker, Jr. | 128/419 PG |

OTHER PUBLICATIONS

Webb et al., "Improved Method for Evaluating Ventriculoatrial Conduction Before Implantation of Atrial-Sensing Dual Chamber Pacemakers", JACC, vol. 5, No. 6 (Jun. 1985), pp. 1395–1402.

Primary Examiner—William E. Kamm
Assistant Examiner—Timothy Keegan
Attorney, Agent, or Firm—Bryant R. Gold

[57] ABSTRACT

An atrial tracking dual-chamber pacemaker and method of use for reducing the risk of initiating a pacer mediated tachycardia (PMT), and breaking such a PMT if once started. The pacemaker includes means for sensing a premature ventricular contraction (PVC). The pacemaker operates in a conventional manner unless a PVC is sensed. If a PVC is sensed, in accordance with one embodiment, an extended atrial refractory period is triggered in an attempt to block any retrograde atrial events resulting from the PVC. This is followed by an atrial alert time window. After a prescribed A-V delay subsequent to the timing out or other termination of the atrial alert time window, a ventricular stimulation pulse is generated, unless prior ventricular activity is sensed that inhibits such ventricular stimulation pulse. In accordance with another embodiment, the sensing of a PVC triggers, after a suitable refractory period, a retrograde sense period during which any sensed atrial electrical activity is presumed to be a retrograde event. Appropriate steps are taken in order to deal with the retrograde event to prevent its occurrence from triggering a PMT. If a PMT has started, a prescribed number of cycles of the PMT are counted, after which the same action used in response to a sensed PVC is triggered, which action disrupts the rhythm of the PMT so as to break it. If the PMT is not broken with the first attempt, the PVC response is recurringly generated after a prescribed number of subsequent PMT cycles.

56 Claims, 9 Drawing Sheets

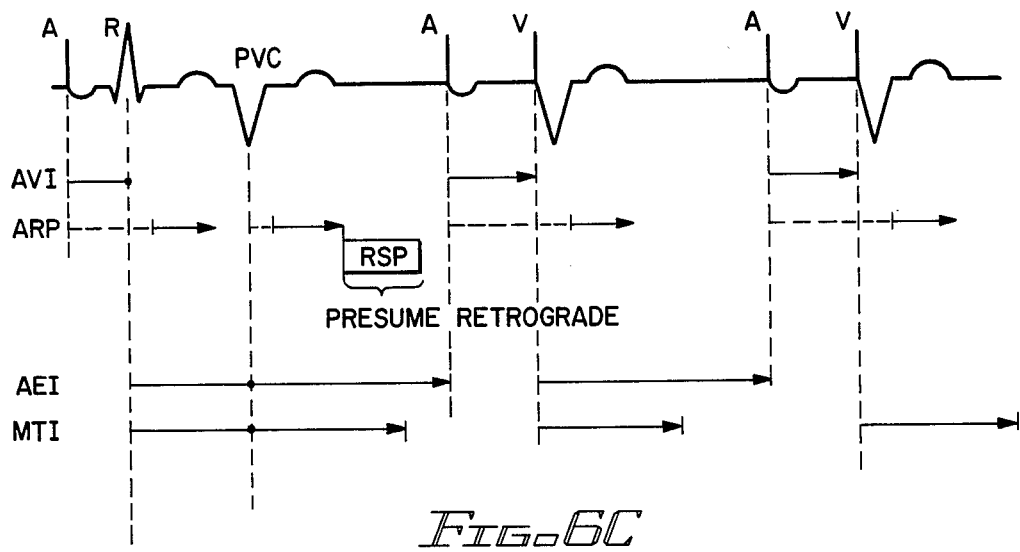
_Fig. 6C_
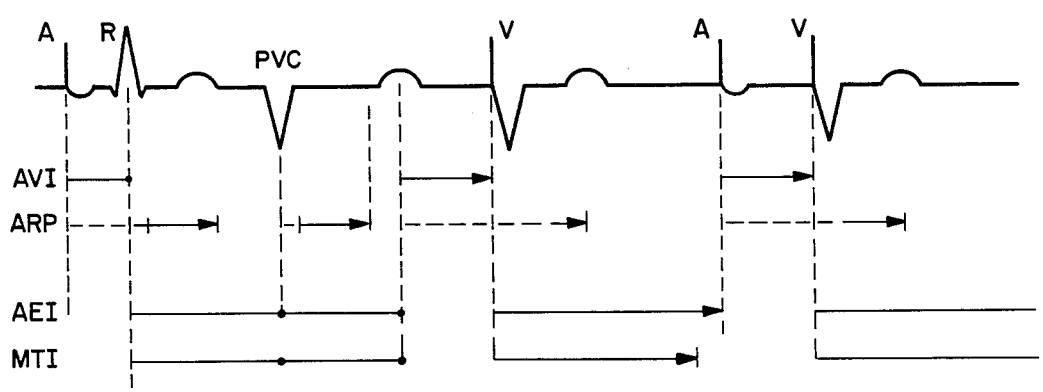
_Fig. 6D_
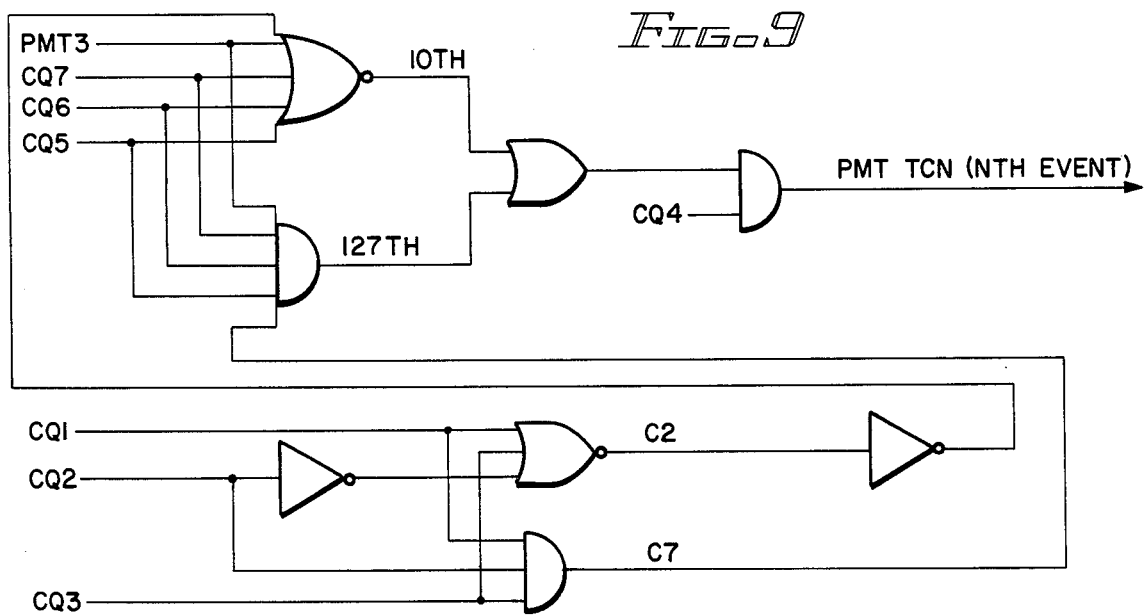
_Fig. 9_

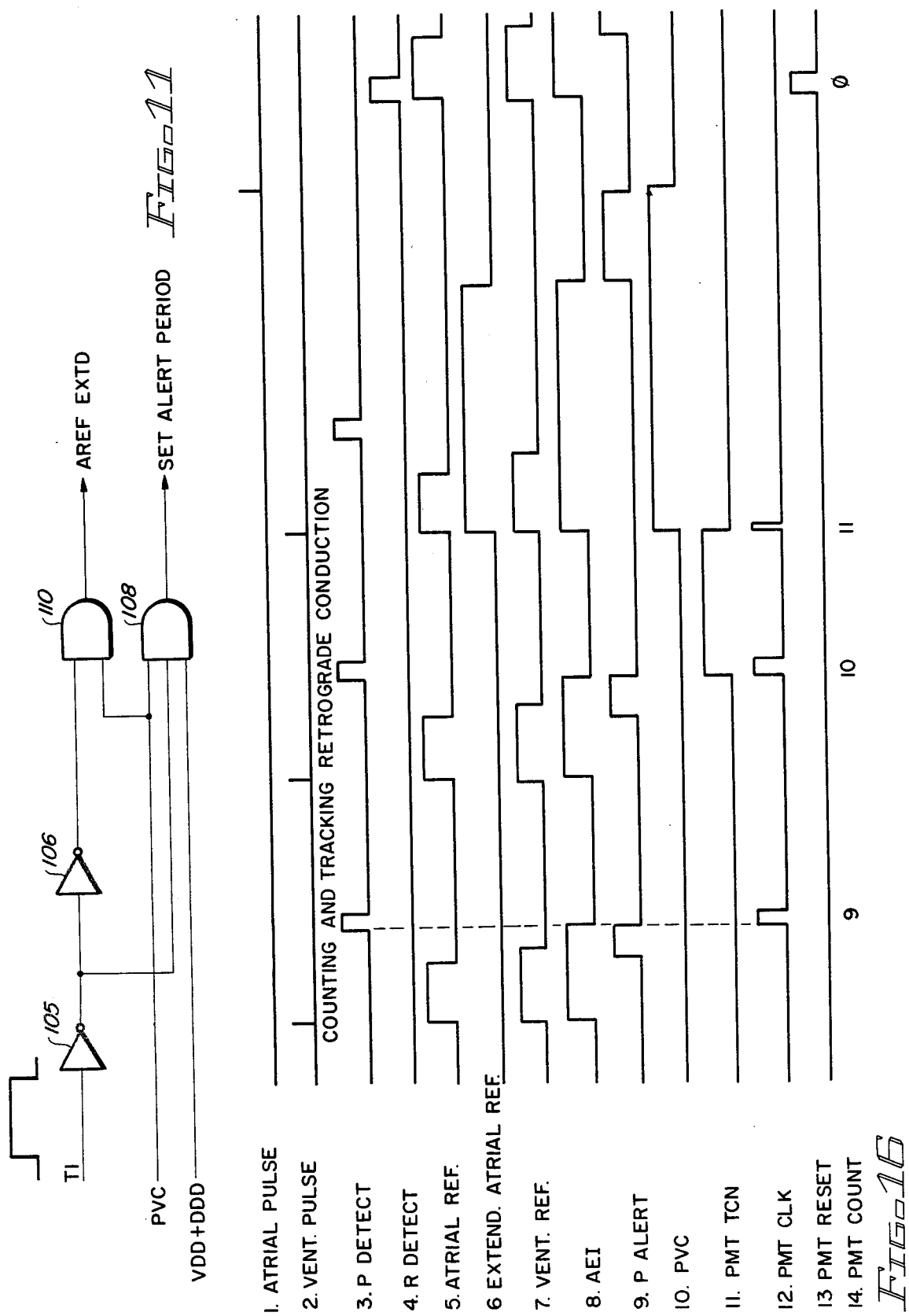

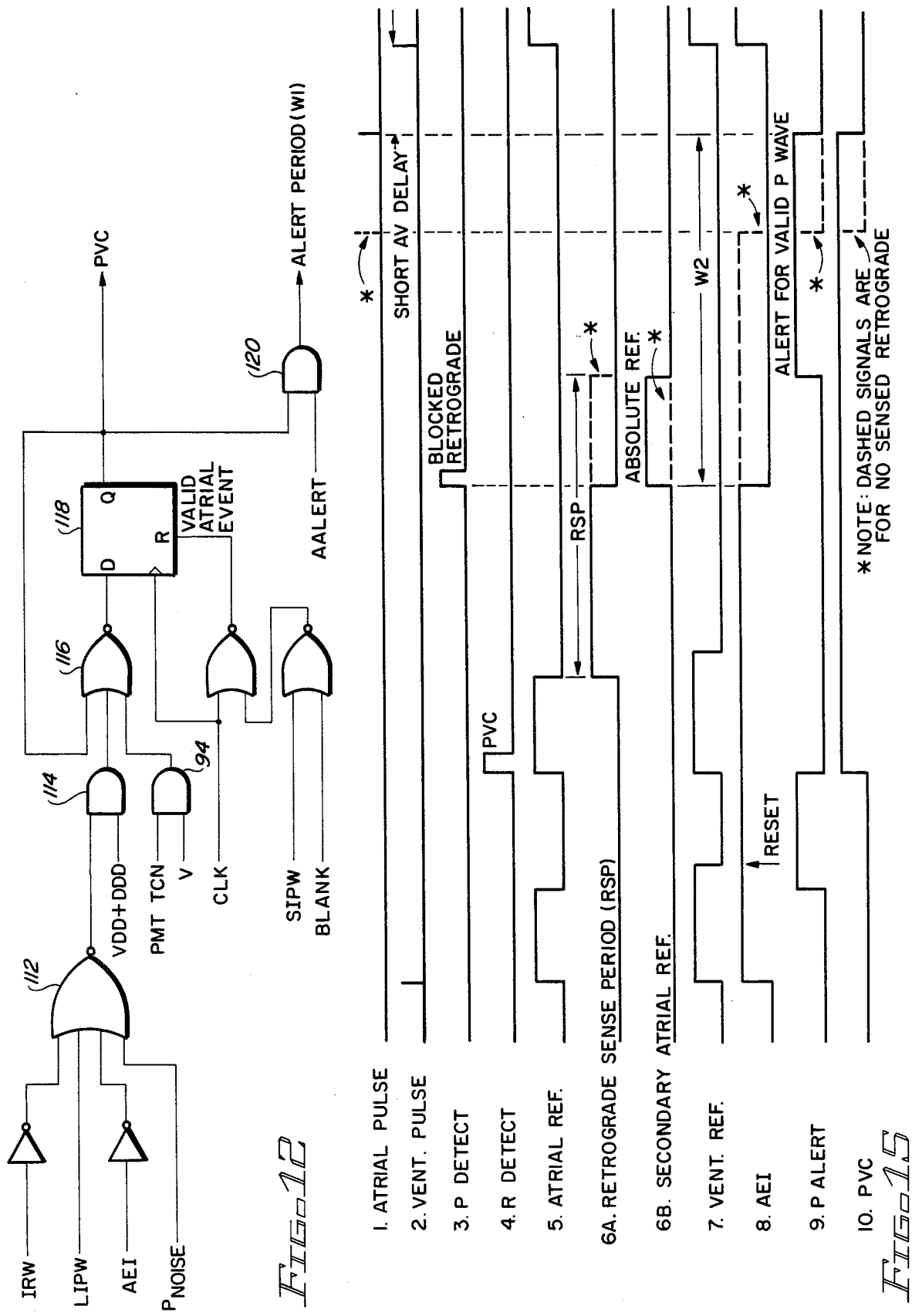

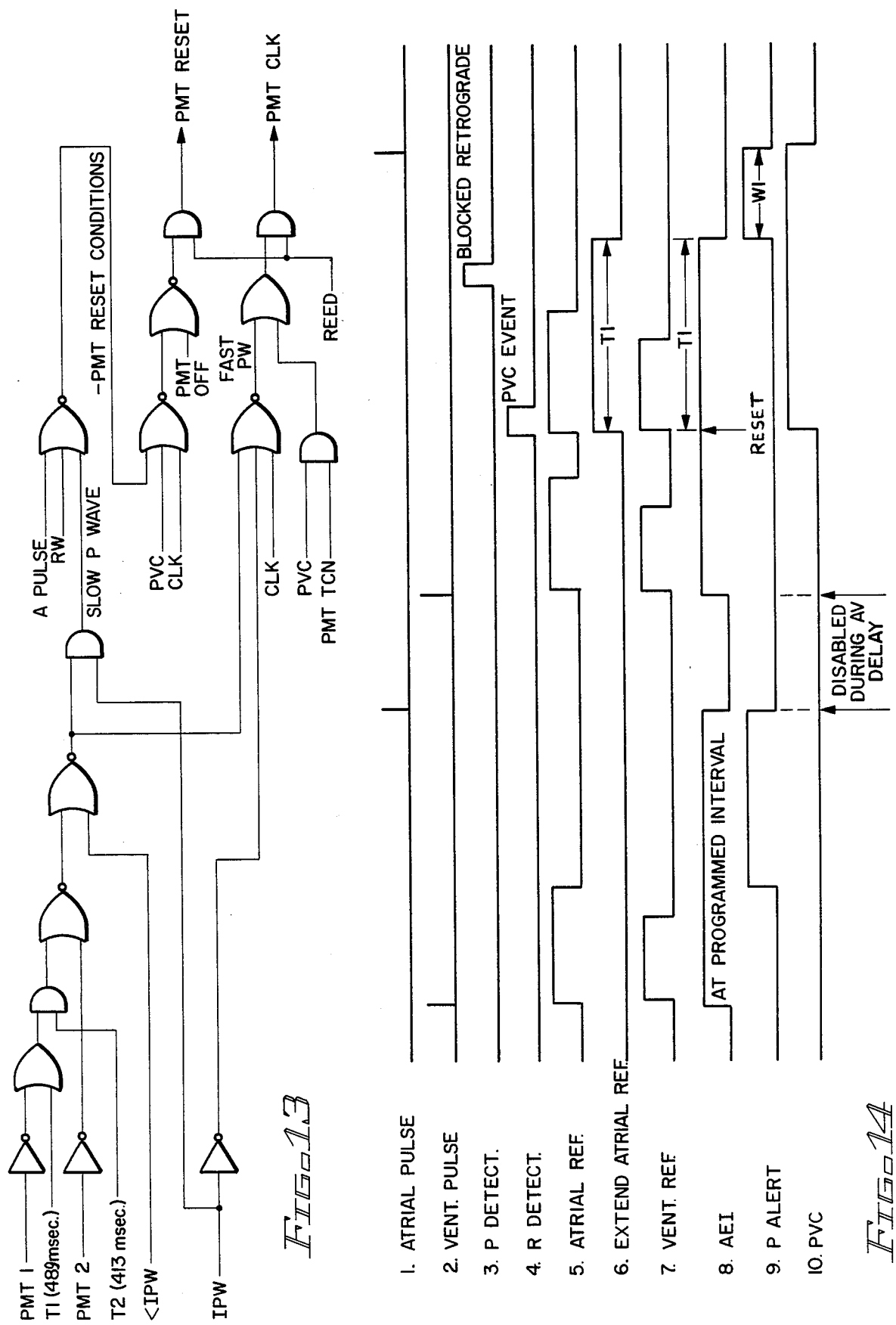

PACEMAKER HAVING PVC RESPONSE AND PMT TERMINATING FEATURES

This invention relates to cardiac pacemakers, and more particularly to an implantable, programmable, dual-chamber cardiac pacemaker that responds to the occurrence of a premature ventricular contraction (PVC) so as to reduce the likelihood that such PVC will trigger a pacer mediated tachycardia (PMT). Further, the invention relates to a pacemaker having the capability of effectively terminating such a PMT if one is initiated.

BACKGROUND OF THE INVENTION

A tachycardia is a very rapid rhythm or rate of the heart. In recent years, with the advent of multi-mode dual-chamber demand-type cardiac pacemakers, it has been discovered that the pacemaker itself, in responding to sensed electrical activity in the heart (which electrical activity may be premature or the result of retrograde conduction) may be responsible, at least in part, for triggering and/or maintaining a tachycardia in those patients who have retrograde conduction. In such an instance, the resulting tachycardia is referred to as a pacer mediated tachycardia (PMT) because it is the operation of the pacemaker that sustains the tachycardia, typically at the maximum tracking rate of the pacemaker.

In order to efficiently perform its function of a pump, the heart must maintain a natural AV synchrony. The term "AV syncrony" relates to the sequential timing relationship that exists between the contractions of the atria and the ventricles. In a given heart cycle or beat, these contractions are typically manifest or measured by sensing electrical signals or waves that are attendant with the depolorization of heart tissue, which depolorization immediately precedes (and for most purposes can be considered concurrent with) the contraction of the cardiac tissue. These signals or waves can be viewed on an electrocardiogram and include a P-wave, representing the depolorization of the atria; the QRS wave (sometimes referred to as an R-wave, the predominant wave of the group), representing the depolorization of the ventricles; and the T-wave, representing the repolarization of the ventricles. (It is noted that the atria also are repolarized, but this atrial repolarization occurs at approximately the same time as the depolorization of the ventricles; and any electrical signal generated by atrial repolarization is generally minute masked out by the much larger QRS-wave on the electrocardiogram.)

Thus, it is the P-QRS-T cycle of waves that represents the natural AV synchrony of the heart. These waves, including the timing relationships that exist therebetween, are carefully studied and monitored through conventional ECG techniques whenever the operation of the heart is being examined.

Multiple-mode, dual-chamber, demand-type, cardiac pacemakers are designed, insofar as possible, to maintain an AV syncrony for damaged or diseased hearts that are unable to do so on their own. This is realized by placing electrodes in both the right atrium and right ventricle of the heart. These electrodes are coupled through intravenous and/or epicardial leads to sense amplifiers housed in an implanted pacemaker. Electrical activity occurring in these chambers can thus be sensed. When electrical activity is sensed, the pacemaker assumes that a depolorization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing. This stimulation pulse causes or forces the desired depolorization and contraction of the indicated chamber to occur. Hence, by first sensing whether a natural depolorization occurs in each chamber, and by second stimulating at controlled time intervals each chamber with an external stimulation pulse in the absence of a natural depolorization, the AV synchrony of the heart can be maintained.

Unfortunately, there are many operating constraints and conditions of the heart that complicate the operation of a demand-type pacemaker. (A demand-type pacemaker is one that provides a stimulation pulse only when the heart fails to produce a natural depolorization on its own within a prescribed escape interval.) For example, there are certain time periods following a depolorization of cardiac tissue (prior to repolarization) when the application of an external electrical impulse is ineffective—that is, it serves no useful purpose, and thus represents an unneeded expenditure of the pacemaker's limited energy. Therefore the application of stimulation pulses during these time periods is to be avoided. Further, it is not uncommon for extraneous electrical signals or noise to be present. These electrical noise signals may be of sufficient amplitude to be sensed by the sensing amplifiers of the pacemaker, which sensing can "fool" the pacemaker into thinking that it has sensed electrical activity associated with a natural depolorization of the heart tissue, when in fact all that it has sensed is noise.

In order to prevent the pacemaker from generating and delivering stimulation pulses during the natural refractory time period of the heart, or from sensing and responding to electrical noise, it is common in the art to include within the pacemaker a timer circuit that defines a refractory period immediately subsequent to the sensing of major electrical activity, or immediately subsequent to the generating of an electrical stimulus. During this pacer-controlled refractory period, all of the sensing and pulse generating circuits of the pacemaker are inoperable. Following this refractory period, the sensing and pulse generating circuits are again operable and the normal sensing/pacing functions of the pacemaker continue.

One of the conditions of the heart that complicates the operation of a pacemaker is the occurrence of a premature ventricular contraction, or PVC. A PVC is a ventricular contraction that occurs out of sequence, i.e., after a previous ventricular contraction but prior to a succeeding atrial contraction. Needless to say, a recurring PVC may greatly disrupt the AV synchrony of the heart. Moreover the occurrence of an isolated PVC—an occurrence that is quite common—may, if a pacemaker is employed, "fool" the pacemaker into responding as though the PVC were a normal ventricular contraction. This is not all bad, inasmuch as any ventricular contraction, premature or otherwise, represents a major cardiac event from which most timing functions of the pacemaker are appropriately referenced. However, as set forth below, unless some sort of precautionary measures are taken, the occurrence of a PVC can combine with the otherwise normal operation of a dual chamber, multi-mode pacemaker operating in either the DDD or VDD mode of operation to trigger a pacer mediated tachycardia, or PMT.

To understand how a PMT may be triggered by the single occurrence of a PVC, it is necessary to have a basic understanding of retrograde conduction. Retrograde conduction is a condition of the heart whereby an impulse resulting from a spontaneous or paced contraction of the ventricle propagates or conducts into the atrium where it causes an atrial depolarization. This ventricle-to-atrium (VA) type of conduction is backwards from the normal atrium-to-ventricle (AV) type of conduction that occurs within the heart during normal operation, hence the term "retrograde" is employed to describe it.

When a PVC occurs in a patient having a pacemaker, it is quite possible that through retrograde conduction the PVC will also cause the atrium to contract a short time thereafter. The pacemaker, sensing the electrical activity of the atrium, responds to this retrograde atrial contraction as though it were a normal atrial contraction in a regular cardiac sequence. That is, in response to the sensed atrial activity which the pacemaker assumes is a natural or sinus P-wave, the pacemaker may generate a ventricular stimulation pulse for delivery to the ventricle a prescribed time period later, designated as the A-V time period, (which A-V time period, for purposes herein, may be extended by an appropriate factor to deal with Wenckeback behavior). This ventricular stimulation pulse causes the ventricle to contract at a time much earlier in the cardiac cycle than it would have otherwise. In the presence of retrograde conduction, a stimulating impulse resulting from this ventricular contraction may conduct into the atrium and cause an atrial contraction, and the whole process repeats itself, thereby causing a tachycardia or rapid heart rhythm truly mediated by the pacemaker. The mechanism that sustains this tachycardia or rapid heart rhythm is: (1) the retrograde path from the ventricle to the atrium, causing the atrium to contract a short time after every ventricular contraction, and (2) the anterograde or forward path from the atrium to the ventricle, provided by the pacemaker, causing the ventricle to receive a stimulation pulse a prescribed time subsequent to the contraction of the atrium. As explained previously, this type of tachycardia, wherein one of the paths that sustains it is provided by the pacemaker, is referred to as a pacer mediated tachycardia, or PMT. Disadvantageously, as is evident from the description given above, under the right circumstances the occurrence of a single PVC can trigger a PMT. A PMT is typically characterized by the heart beating at its maximum tracking rate as set by the pacemaker. (Note: all dual chamber pacemakers which track atrial events typically employ timing circuits that set an upper limit at which pacing pulses will be provided. This upper limit, referred to as the maximum tracking rate, is the rate at which a PMT is generally sustained, although in some instances the rate of a PMT may be lower than the maximum tracking rate.)

To prevent a PVC from triggering a PMT, it is known in the art to extend the pacemaker-generated atrial refractory period upon detection of a PVC. That is, if a PVC is defined as a sensed ventricular event that occurs prior to an atrial event in the normal cardiac cycle, then the logic circuits of the pacemaker can detect when a PVC occurs. Upon such detection, the atrial refractory period, present in each cardiac cycle, is automatically extended a prescribed amount. For example, the Cosmos pacer manufactured by Intermedics, Inc. of Freeport, Tex., extends the atrial refractory period by a programmable amount upon the sensing of each PVC. Similarly, the AFP pacemaker manufactured by Pacesetter Systems, Inc., of Sylmar, Calif., extends the atrial refractory period by a fixed extension period that is equal to the entire remaining interval within the cardiac cycle. The reason for extending the atrial refractory period, as taught in the art, is to prevent the subsequent retrograde atrial depolarization, if present, from being sensed, thereby "controlling" the pacemaker to operate as though no atrial activity had occurred. This means that the next event in the cardiac cycle following the ventricular contraction would be the generation of an atrial stimulus. The teachings of the art are that the extension of the atrial refractory period should be extended a sufficient amount so that any retrograde atrial event will fall within this extension, thereby precluding such retrograde atrial event from being sensed.

Unfortunately, it has recently been learned that extension of the atrial refractory period can itself create the conditions necessary to start a PMT. For example, the occurrence of a PVC, which occurrence causes the atrial refractory period to be extended, may not cause a retrograde atrial contraction. If such is the case, there is a chance that a natural or sinus P-wave will fall near the end of the extended atrial refractory period. However, this P-wave will not be sensed by the pacemaker because it occurs during the pacer-defined refractory time period. Hence, the pacemaker continues to operate as though no sinus P-wave had occurred, generating an atrial stimulus, followed by a ventricular stimulus one A-V delay later. However, the atrial stimulus may not be effective due to the natural refractory period of the heart as a result of the nonsensed sinus P-wave. This results in an effective prolongation of the A-V delay (sinus P-wave to paced ventricular stimulus), which prolongation enhances the likelihood that retrograde conduction will occur. If retrograde conduction is present at the subsequent ventricular stimulus, a PMT may be started. Because of this possibility there is a need in the art for a pacemaker response to a PVC that reduces the likelihood of triggering a PMT.

Other mechanisms exist for triggering a PMT besides a PVC, such as tracking of electrical signals produced by muscle movement (myopotentials) or premature atrial contractions. Accordingly, there is also a need in the pacemaker art for a means of breaking a PMT once started. One approach known in the art for breaking a PMT is to drop one ventricular stimulus for every 16 beats at the maximum tracking rate. While this may be effective in some instances, it is not always effective. For example, as used in the art, a ventricular stimulus is dropped only when the pacemaker is operating at its maximum tracking rate. While the preponderance of PMT cases are at the maximum tracking rate, it is conceivable that a PMT could occur at a different rate. Further, by dropping the ventricular stimulus completely and going an additional full cycle, the pause in ventricular stimulus becomes sufficiently long so as to increase the possibility of another PVC. This PVC may then again immediately restart the PMT that was just terminated.

SUMMARY OF THE INVENTION

The present invention provides a dual-chamber demand-type pacemaker, and method of operating the same, that reduces the risk of initiating a pacer mediated tachycardia (PMT), and that breaks such a PMT if once started. The pacemaker of the present invention includes means for sensing a premature ventricular contraction (PVC). The pacemaker operates in a conventional atrial tracking manner (typically DDD or VDD modes of operation) unless a PVC is sensed. If a PVC is sensed, the atrial escape interval land the atrail refractory period are appropriately adjusted as described below. This is in contrast to prior art devices wherein only the atrial refractory period is adjusted.

In accordance with a first embodiment of the invention, the sensing of a PVC triggers an extended atrial refractory period, followed by an atrial alert period or window. Atrial activity occurring within the extended atrial refractory period is not sensed. atrial activity occurring within the atrial alert window is sensed, and inhibits any atrial stimulation pulse that would otherwise be generated. If no atrial activity is sensed during the atrial alert time window, an atrial stimulation pulse is generated at the conclusion thereof. In either event, after a prescribed A-V delay subsequent to the sensing of atrial activity, or the failure to sense atrial events within the V-A interval, a ventricular stimulation pulse is generated, unless prior sensed natural ventricular activity inhibits such a generation in accordance with the operation of a conventional demand-type pacemaker.

Advantageously, the atrial alert window following the extended atrial refractory period assures that no stimulation pulse will be provided to the atrium at a time when the atrium may be in its natural refractory state, as might otherwise happen if a sinus P-wave occurs at the end of the extended atrial refractory period. Further, the maintaining of a prescribed A-V delay between the atrial stimulus and the subsequent ventricular stimulus minimizes the likelihood that retrograde conduction will subsequently occur. Hence, even though a sinus P-wave may have previously occurred, this event is followed by an atrial stimulus, which atrial stimulus is applied a sufficient time following the sinus P-wave to assure its effectiveness, and the ventricular stimulus, if needed, is applied a prescribed A-V delay thereafter. This sequence avoids the undesirable prolongation of the A-V delay wherein the delay is caused by an ineffective atrial stimulus applied during the natural refractory period of the atrium. By avoiding prolonged A-V delays, long V—V delays are also minimized, thereby reducing the likelihood of occurrence of retrograde conduction, which in turn reduces the risk of initiating a PMT.

In a second embodiment of the invention, the sensing of a PVC triggers an atrial refractory period followed by a retrograde sense period. During this retrograde sense period atrial activity can be sensed. If atrial activity is sensed, a prescribed alert time window is triggered (this alert time window includes both refractory and alert portions), following which an atrial stimulus is generated if no subsequent atrial or ventricular event is sensed. If atrial activity is not sensed during the retrograde sense period, the prescribed alert time window is not initiated. Thus the prescribed atrial stimulus and A-V delay follow the end of the prescribed alert time window, if one is triggered; or, if a prescribed alert time window is not triggered, the A-V delay follows the normal V-A timing. After the A-V interval a ventricular stimulus will be generated, unless such stimulus is inhibited by the sensing of ventricular activity, as in conventional demand-type pacer operation.

As is evident from the above description, in the first embodiment the atrial refractory period is extended in response to a sensed PVC for the purpose of masking out any atrial retrograde events. This extended refractory period is followed by a fixed alert period, which effectively functions as an extension of the atrial escape interval and which prevents a pacer-generated atrial stimulus from being applied to the atrium during a natural refractory period (as is the case where an atrial event occurs near the end of the extended refractory period). In the second embodiment, a retrograde sense period is added after the refractory period in response to a sensed PVC for the purpose of sensing any atrial retrograde events. Once sensed, these retrograde events are dealt with in an appropriate manner in order to minimize the likelihood that a PMT will be triggered.

A third embodiment of the invention contemplates suspending the maximum tracking interval, MTI, if atrial activity, following a PVC, is sensed subsequent to the atrial refractory period. Such atrial activity is presumed to be a valid P-wave from which an A-V interval is triggered. If no atrial event is sensed at this time, then normal pacemaker operation continues, meaning that an atrial stimulus is generated at the conclusion of the appropriate atrial escape interval.

In a fourth embodiment of the invention, available for use with any of the above-described embodiments, in response to a sensed PVC, and in addition to the other responses described above, the A-V interval is shortened slightly so as to make the ventricular stimulus occur a little sooner, thereby avoiding long A-V intervals, and helping to prevent long V—V intervals.

The method of operating a pacemaker according to the present invention includes as a first step sensing the occurrence of a PVC. For the first embodiment, the subsequent steps include: extending the atrial refractory period a prescribed amount, inserting an atrial alert time period or window subsequent to the timing out of the extended atrial refractory period, and initiating a prescribed A-V delay subsequent to the timing out of the atrial alert time window or subsequent to the sensing of an atrial event during the atrial alert time window. For the second embodiment, the subsequent steps of the method include: adding a retrograde sense period after the refractory period, defining any sensed atrial event occurring during this retrograde sense period as a retrograde event, initiating a prescribed alert time period in response to the sensing of a retrograde event, defining any sensed atrial event occurring during this prescribed alert time period as a valid P-wave, and initiating a prescribed A-V delay subsequent to the sensing of a valid P-wave or the timing out of the prescribed alert time period. For the third embodiment, the subsequent steps include: suspending the MTI after any sensed atrial event following a PVC and initiating a prescribed A-V delay subsequent to such sensing. If no P-wave is sensed, normal pacemaker operation continues.

The method of breaking a pacer mediated tachycardia, if one is initiated, in accordance with the present invention includes: counting the occurrence of PMT cycles; and triggering, in response to reaching a prescribed PMT cycle count, the extended atrial refractory period and atrial alert time window (as herein described in connection with the first embodiment), or the retrograde sense period and prescribed alert time period (as herein described in connection with the second embodiment), or other appropriate time periods (as used, for example, in connection with the third embodiment), which action disrupts the rhythm of the PMT so as to break it. If the PMT is not broken with the first attempt, the triggering of the various retrograde, sense, or other time periods is recurringly generated after a prescribed number of subsequent PMT cycles.

BRIEF DESCRIPTION OF THE DRAWINGS

The above and other objects, features, and advantages of the present invention will be more apparent from the more particular description thereof presented in conjunction with the following drawings wherein:

FIGS. 6B and 6C are composite timing diagrams illustrating the effect of a second embodiment of the PVC response of the present invention;

FIG. 6D is a composite timing diagram illustrating the effect of a third embodiment of the PVC response of the present invention;

FIG. 9 is a logic diagram of the Nth Count Logic of FIG. 8 for a specific embodiment of the invention;

FIG. 11 is a logic diagram of the circuitry used to extend the atrial refractory period;

FIG. 12 is a logic diagram of the PVC Detect Logic of FIG. 8;

FIG. 13 is a logic diagram of the PMT window and PMT Reset Window Logic of FIG. 8;

FIG. 14 is a logic timing diagram illustrating the operation of the circuits of FIGS. 8–13 in responding to a PVC which operation corresponds to the timing diagram of FIG. 6A;

FIG. 15 is a logic timing diagram illustrating an alternative operation of the circuits of FIGS. 8–13 in responding to a PVC, which operation corresponds to the timing diagram of FIG. 6B; and FIG. 16 is a logic timing diagram showing the operation of the circuits of FIGS. 8–13 when terminating a PMT after n counts.

DETAILED DESCRIPTION OF THE INVENTION

The following description is of the best presently contemplated mode of carrying out the invention. This description is not to be taken in a limiting sense but is made for the purpose of describing the general principles of the invention. The scope of the invention should be determined with reference to the appended claims.

Figure 1:
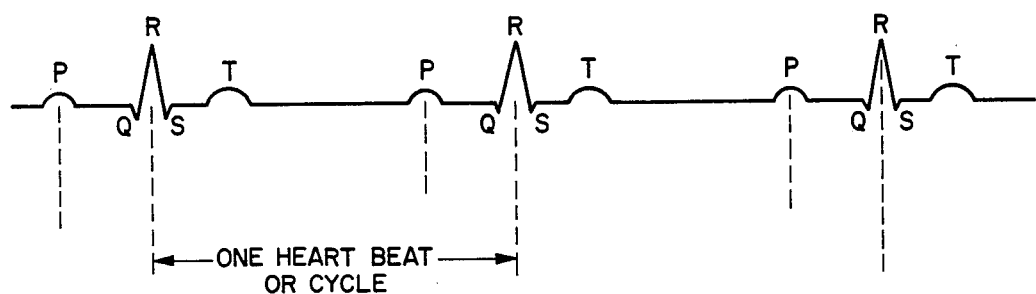
FIG. 1 is a typical ECG-type waveform illustrating the normal AV synchrony of the heart.

Referring to FIG. 1, there is shown a typical ECG-type waveform illustrating the normal A-V synchrony of a heart. Such waveforms may be obtained using conventional skin-electrode ECG techniques. alternatively, intercardiac ECG features of modern pacemakers may provide similar ECG information through the use of the telemetry features of such pacemakers. Beginning at the left of the waveform there is shown a P-wave. This P-wave represents the electrical activity coincident with the depolarization of the atria of the heart. As indicated previously, depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS wave (often referred to as simply an R-wave) is a very important time interval in the operation of the heart because it represents the time needed for the blood to flow from the atria into the ventricles. The R-wave is followed by a T-wave, which wave represents the electrical activity associated with the repolarization of the ventricles. As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat could, of course, be measured relative to any point within the heart cycle, such as between succeeding T-waves.

The important point for purposes of the present application to recognize is that a certain AV synchrony must occur if the heart is to function efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricle. If the depolarization of the atria or ventricles do not occur naturally, then a pacemaker may be employed to provide stimulation pulses to these respective heart chambers, in order to trigger the required depolarization/contraction at the appropriate time periods of the heart cycle.

Figure 2:
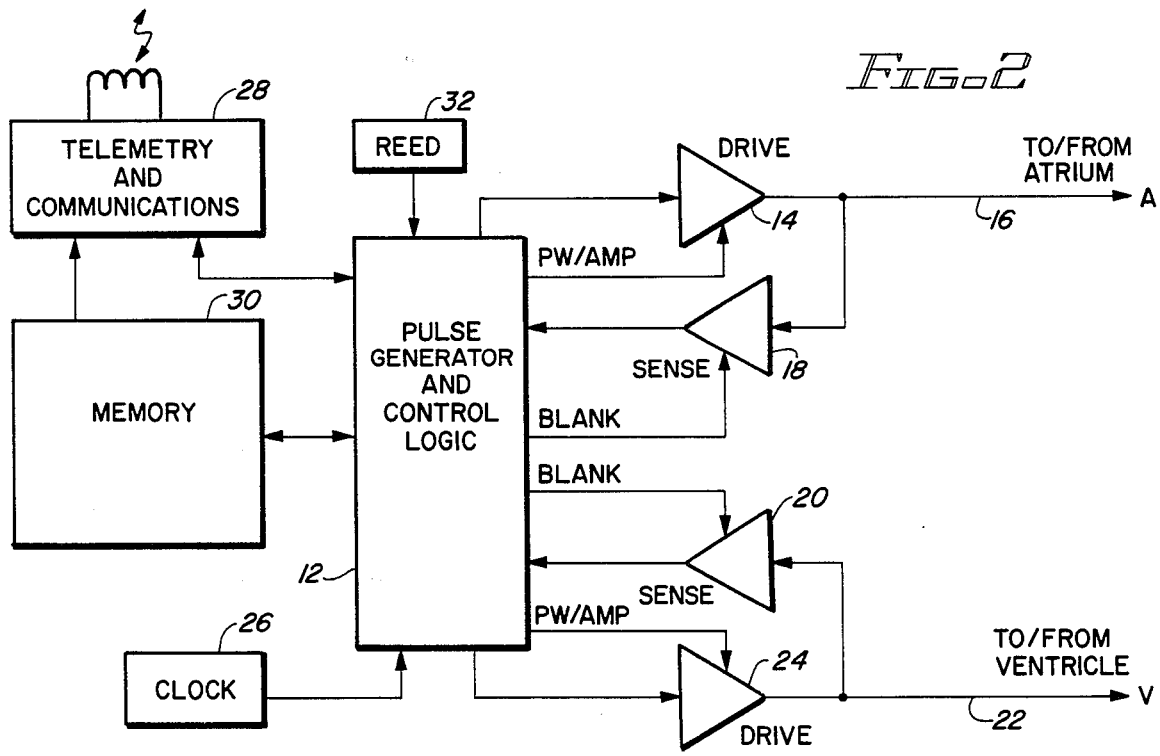
FIG. 2 is a block diagram of an implantable, programmable, dual-chamber pacemaker.

Referring next to FIG. 2, a block diagram of a typical atrial tracking dual-chamber pacemaker is illustrated. Pulse Generator and Control Logic 12 generates the appropriate timing sequences and stimulation pulses for delivery to the heart. Stimulation pulses are delivered to the right atrium of a heart (not shown) through an atrial drive amplifier 14 and an atrial lead or conductor 16. This same atrial lead 16 is connected to an atrial sense amplifier 18. This sense amplifier 18 monitors the electrical activity of the atrium to determine if a sinus P-wave, representing the natural depolarization of the atrium, has occurred. If such sinus atrial activity is sensed, then the Pulse Generator 12 inhibits the stimulation pulse provided to the drive amplifier 14 and provides for a tracked ventricular stimulus after a predetermined time period (referred to as the sensed AV delay). However, if after a prescribed period of time, typically referred to as the atrial escape interval, a sinus P-wave has not been sensed, then the pulse generator 12 delivers a stimulation pulse, through the drive amplifier 14, to the atrium over lead 16. The pulse width and amplitude (PW/AMP) of this stimulation pulse are controlled by the pulse generator and control logic 12.

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate ventricular escape interval, then the Pulse Generator and Control Logic 12 generates a ventricular stimulation pulse of a prescribed pulse width and amplitude, delivered through the drive amplifier 24, in order to cause the desired ventricular contraction.

Clock circuitry 26 provides the basic clock signal from which the pulse generator and control logic 12 operates. Telemetry and communications circuitry 28 provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or cardiologist to monitor the activity of the heart without the use of external skin electrodes. A magnetic reed switch 32 is also typically employed with implanted pacemakers in order to control the programmable functions of the device. With a suitable programming apparatus in place, the attending physician or cardiologist can effectuate any desired changes in the operation of the pacemaker by sending appropriate control signals and commands over the telemetry and communications circuitry 28.

Figure 3A:
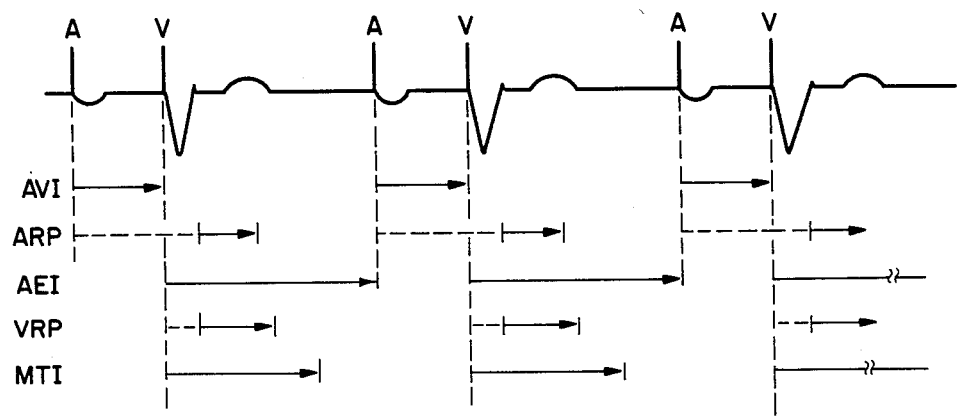
FIG. 3A is a composite timing diagram illustrating how the AV synchrony of the heart is maintained when both atrial and ventricular stimulation pulses are provided to the heart by a dual-chamber pacemaker.

Referring next to FIG. 3A, a composite timing diagram illustrating the operation of a typical demand-type, dual-chamber pacemaker is illustrated. In this timing diagram, the stimulation pulses generated by the pacemaker are illustrated as a narrow spike labeled with either an A (for an atrial stimulation pulse) or a V (indicating a ventricular stimulation pulse). Further, the response of the heart to an applied stimulation pulse is indicated in the figures as having an opposite polarity from that shown in FIG. 1. (In FIG. 1, the heart responds without the application of a stimulation pulse.) This is done to clearly distinguish in the figures naturally occurring events of the heart from pacer-induced events.

Included in the timing diagram of FIG. 3A, are representations of the various timing intervals that are generated by the pulse generator and control logic 12 (FIG. 2). Many of these time intervals are programmable, meaning that the length of such intervals can be varied by sending appropriate control signals over the telemetry and communications circuitry 28 to the memory circuits 30 of FIG. 2. As those skilled in electronic art will recognize, by loading an appropriate data word into a prescribed memory location, which data word can in turn be subsequently loaded into an appropriate counter of the pulse generator and control logic 12, a basic clock signal can then be used to clock this counter until the desired count is reached, at which time a terminal count signal is generated to indicate the end of the desired time interval. By merely changing the value of the data word that is loaded into memory, the length of the time interval can thus be varied or programmed to a desired value.

The time intervals shown in the timing diagrams that follow are indicated by a horizontal line. If the time interval has "timed out"—that is, if it has reached its terminal count—an arrowhead is place on the horizontal line, pointing to the point in time at which the time interval terminates. (Note: in all of the timing diagrams used herein, the horizontal axis represents the time axis.) It is noted that the timing drawings are not necessarily drawn to scale, nor with linear horizontal or vertical axes. If, however, a sensed electrical event occurs prior to the termination of a given interval, which event inhibits the generation of a stimulation pulse (or alters some other operation of the pacemaker) then a dot is placed on the horizontal line indicating the point in time at which the sensed event terminates that particular interval.

Shown in FIG. 3A, and in the similar timing diagrams provided herein, are five basic time intervals. These are: (1) the A-V interval, or AVI, representing the time interval between the atrial stimulation pulse and the ventricular stimulation pulse (sometimes referred to as the pacemaker A-V delay); (2) the atrial refractory period, or ARP, representing the time interval subsequent to the generation of an atrial stimulation pulse or sensed atrial event during which the atrial sensing circuits are disabled; (3) the atrial escape interval, or AEI, representing the time interval during which in the absence of naturally occurring atrial or ventricular activity, an atrial stimulation pulse will be generated and delivered to the atrium; (4) the ventricular refractory period, or VRP, representing the interval during which the ventricular sense amplifier 20 (FIG. 2) is disabled; and (5) the maximum tracking interval, or MTI, representing the interval where P-waves will be tracked up to the maximum tracking rate. (The MTI+AVI thus define for purposes of this application, the shortest possible time period of a cardiac cycle, and hence, the maximum possible paced ventricular rate. In contrast, some prior art pacers include AVI in the MTI interval.)

With the foregoing timing intervals thus defined, the following description of FIGS. 3–6 can be better understood. As indicated previously, in FIG. 3A, there is shown a timing diagram illustrating how a pacemaker is used to maintain a desired AV synchrony of the heart. In FIG. 3A, it is assumed that the heart being stimulated can not provide its own atrial or ventricular contractions at a suitable rate, and that the pacemaker must therefore provide the stimulation pulses required to maintain the desired AV synchrony and/or heart rate.

Accordingly, an atrial pulse A is provided in order to invoke a contraction of the atrium. This event triggers both the A-V interval, AVI, and the atrial refractory period, ARP. A portion of the ARP, designated in the figures as a dashed line, in an absolute refractory period, meaning that the atrial sense amplifier 18 (FIG. 2) is totally blanked or inoperable. A subsequent portion of the ARP, represented in the figures as a solid line, is a relative refractory period, meaning that special processing methods are used (not relevant to the present discussion) in an attempt to distinguish the occurrence of valid P-waves from noise. As indicated in FIG. 3A, at the termination of the AVI, a ventricular stimulation pulse, V, is generated an applied to the heart. This stimulation pulse causes the ventricle to contract, as indicated by the inverted R-wave. The generation of the ventricular stimulation pulse, or V-pulse, also triggers the beginning of the atrial escape interval, or AEI; the ventricular refractory period, or VRP; and the maximum tracking interval, or MTI. At the conclusion of the AEI, there having been no P-waves sensed, an A-pulse is generated in order to produce a contraction of the atrium, thereby initiating the next cycle of the heart. Thus, the events previously described begin again and the cycle repeats itself, with a V-pulse being generated an A-V interval subsequent to the A-pulse, and an A-pulse being generated at a prescribed interval subsequent to the generation of the V-pulse.

Figure 3B:
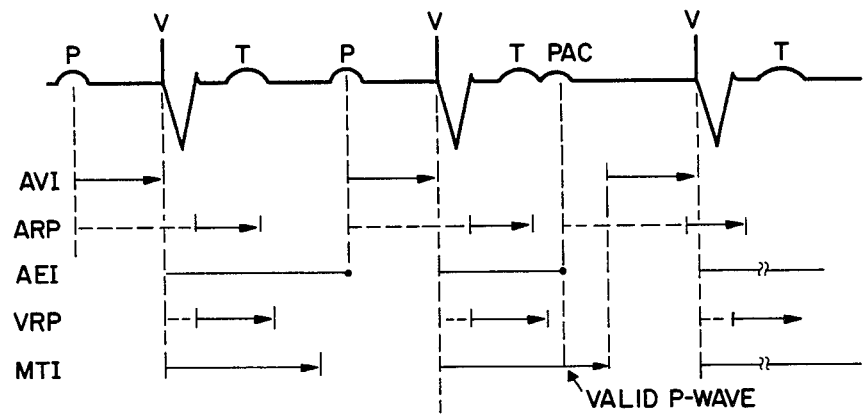
FIG. 3B is a similar composite timing diagram illustrating how A-V synchrony is maintained when only a ventricular stimulation pulse need be provided to the heart, and further illustrates one possible response of a pacemaker to a premature atrial contraction (PAC)

In FIG. 3B, it is seen that a natural or sinus P-wave is present, and hence there is no need for the pacemaker to generate an A-pulse. When the sinus P-wave is sensed, the AVI is initiated, and the pacemaker is alert in order to sense if an R-wave will occur. If an R-wave has not been sensed by the time the AVI times out, then a V-pulse is generated, as indicated. This V-pulse initiates the beginning of the atrial escape interval. Prior to the termination of the AEI, a naturally-occurring P-wave is sensed, indicated by the dot on the AEI line. The sensing of the naturally-occurring P-wave inhibits the generation of an A-pulse, and initiates the beginning of a new AVI, at the conclusion of which another V-pulse is generated. This process continues for so long as the heart continues to generate sinus P-waves, but fails to produce naturally-occurring R-waves.

FIG. 3B further illustrates one possible response of the pacemaker to a premature atrial contraction, or PAC. The premature atrial contraction may be defined, for purposes of this application, as simply a contraction of the atrium that occurs prematurely or early in the normal AV synchrony. The PAC shown in FIG. 3B occurs immediately subsequent to the second T-wave. The pacemaker responds to the PAC as though it were a sinus P-wave. That is, the occurrence of the PAC terminates the atrial escape interval. Further, when a P-wave occurs within MTI, as does the PAC shown in FIG. 3B, a latch circuit is set indicating that the sensed activity is considered a valid P-wave. The setting of this latch causes the A-V interval to be initiated at the end of MTI. At the conclusion of this A-V interval, the V-pulse is generated. Once a V-pulse has been generated, the operation of the pacemaker continues in normal fashion.

Figure 3C:
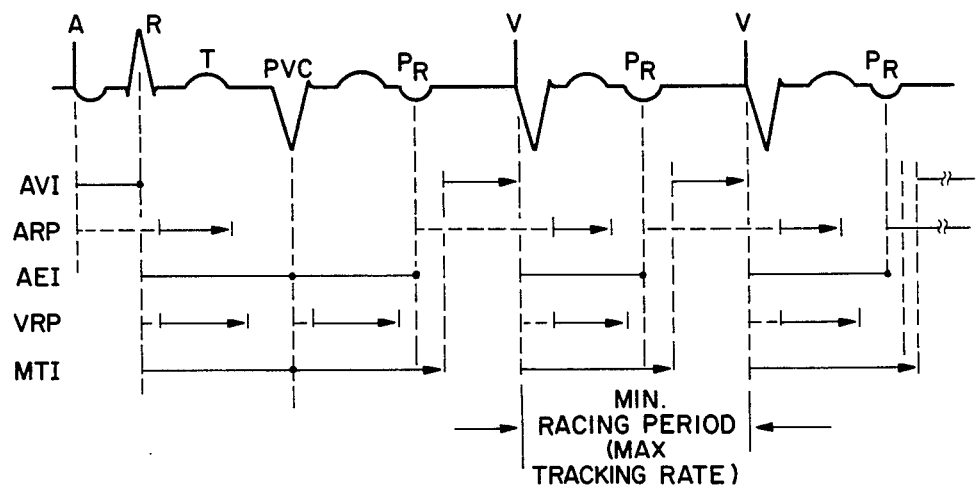
FIG. 3C is a similar timing diagram illustrating one possible way in which a PMT may be triggered.

Referring next to FIG. 3c, a timing diagram is illustrated indicating one way in which a pacer mediated tachycardia, or PMT, may be generated. At the beginning of the sequence shown in FIG. 3C, it is assummed that an A-pulse is provided to stimulate a desired atrial contraction. A short time thereafter, subsequent to the termination of the A-V interval, a naturally occurring R-wave is sensed. Hence, no V-pulse is generated, and the atrial escape interval and other intervals are initiated in normal fashion. However, a short time after the sensing of the R-wave, a premature ventricular contraction, or PVC, occurs. For purposes of illustration, it is assumed in FIG. 3C that the pacemaker can not distinguish between the occurrence of an R-wave and a PVC. That is, the pacemaker simply senses that electrical activity has occurred in the ventricle, and kit therefore assumes that such activity represents a normal ventricular contraction. Of course, as explained previously, a PVC does represent a ventricular contraction; however, it is a ventricular contraction out of sequence—that is, one that occurs subsequent to a preceeding ventricle contraction but prior to the next atrial contraction. As also explained previously, the occurrence of a PVC may, under the right circumstances, through retrograde conduction, cause the atrium to contract. Such a contraction is illustrated in FIG. 3C as a retrograde P-wave, labeled $P_R$. Hence, once the PVC occurs, followed by the retrograde P-wave, $P_R$, a V-pulse is generated a prescribed time thereafter. This prescribed time is at the conclusion of the maximum tracking interval, MTI plus the A-V interval, AVI. In response to the V-pulse, the ventricle contracts, which contraction, through retrograde conduction, again causes a retrograde P-wave to occur. This retrograde P-wave, $P_R$, is again followed by a V-pulse that occurs as soon as possible thereafter, which time is again set by the MTI+AVI intervals. Thus, in this sequence, the heart is paced at the maximum tracking rate, and a PMT is created. The PMT cycle is sustained by the retrograde path through which the retrograde P-wave occurs in response to a ventricular contraction; and the anteograde path, provided by the pacemaker, through which a V-pulse is generated at the conclusion of MTI+AVI intervals.

Figure 4:
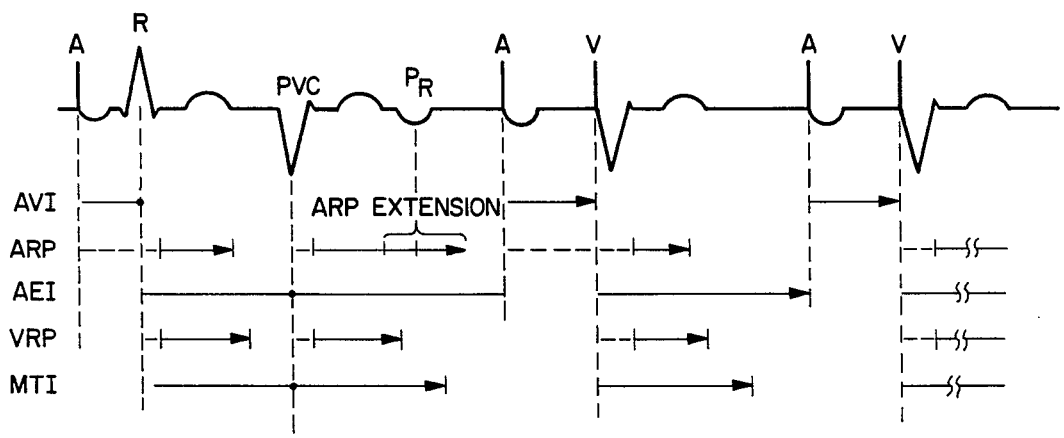
FIG. 4 is a similar timing diagram illustrating how extending the atrial refractory period may preclude the triggering of the PMT shown in FIG. 3C.

Referring next to FIG. 4, there is shown the prior art approach to the solution of the problem illustrated in FIG. 3C. In accordance with the teachings of the prior art, and as mentioned previously, logic circuitry can be employed to recognize the occurrence of a PVC. Once the occurrence of a PVC has thus been identified, then the control logic of the pacemaker extends the atrial refractory period for a prescribed amount. This extension is identified in FIG. 4 as the ARP EXTENSION portion of the atrial refractory period following the occurrence of the PVC. Advantageously, these ARP EXTENSION prevents the retrograde P-wave following the PVC from being sensed by the pacemaker. Accordingly, at the conclusion of the atrial escape interval, an A-pulse will be generated by the pacemaker. Following the A-pulse, a V-pulse will be generated one A-V interval thereafter, unless a natural R-wave occurs prior to the termination of the of the AV interval. Hence, the effect of the extension of the atrial refractory period as illustrated in FIG. 4 is that the atrium contracts twice, once in response to the PVC (through retrograde conduction), and once as a result of the applied A-pulse. Such double contraction of the atrium is, according to the teaching of the prior art, of little consequence so long as it only occurs in one cycle. Further, if the triggering of a PMT can be avoided, the benefits derived therefrom are felt to far outweigh the slight disruption of the AV synchrony that occurs in the one cycle in which the double atrial contraction occurs.

Figure 5:
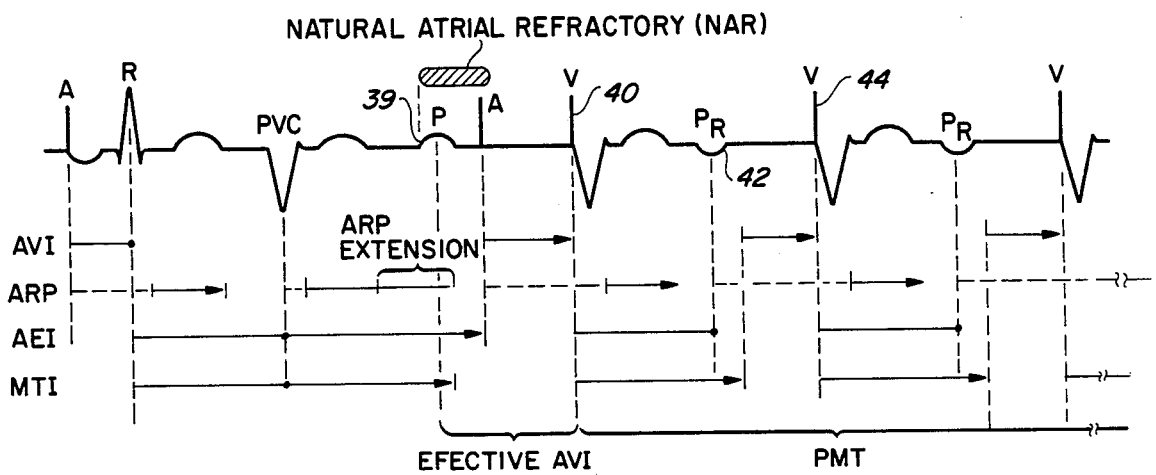
FIG. 5 is a composite timing diagram showing how extending the atrial refractory period, as was done in FIG. 4, may still cause a PMT to be triggered.

Unfortunately, as indicated in the timing diagram of FIG. 5, extending the atrial refractory period can itself create the conditions necessary to trigger a PMT. In FIG. 5, the atrial refractory period has been extended as in FIG. 4. A sinus P-wave occurs during this extended refractory period, but is not sensed by the pacemaker because the sense amplifier of the pacemaker is not operable during this time period. Also shown in FIG. 5, at the upper portion thereof, is a shaded time interval that represents the natural atrial refractory period, or NAR. This is the time period during which the atrial muscle tissue is recovering from a depolarization/contraction, and therefore represents a time during which the atrium is physically incapable of contracting again. This natural atrial refractory period begins as the atrium begins to depolarize. It lasts until the atrial tissue is repolarized, which typically could be 150-300 msec subsequent to the depolarization of the tissue. If, as shown in FIG. 5, the A-pulse is applied to the atrium at the conclusion of the atrial escape interval, as was done in FIG. 4, but also at a time that falls within the natural atrial refractory period, then this A-pulse will be ineffective. The net result of this ineffective action, in addition to representing a needless expenditure of energy from the pacemaker's battery, is that the A-V interval, AVI, as seen by the heart tissue, will be effectively extended or lengthened. This is also illustrated in FIG. 5 as the interval between the sinus P-wave 39 and the subsequently applied V-pulse 40. Lengthening the A-V interval generally enhances the likelihood that retrograde conduction will occur. FIG. 5 depicts the occurrence of such a retrograde P-wave 42 that occurs in response to the ventricular contraction triggered by the application of V-pulse 40. A V-pulse 44 will then be applied as soon as permitted after retrograde P-wave 42, or at the maximum tracking rate. As this process repeats itself, a pacer mediated tachycardia, or PMT, is again present.

Figure 6A:
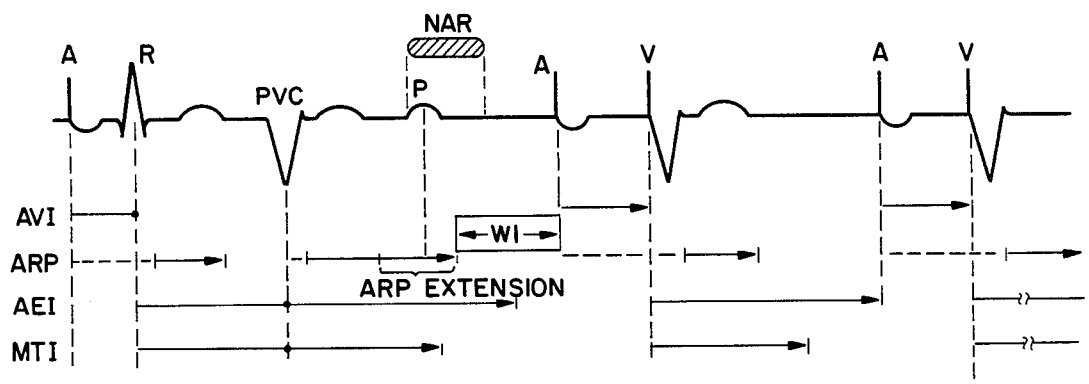
FIG. 6A is a composite timing diagram illustrating the effect of a first embodiment of the PVC response of the present invention.
Figure 6B:
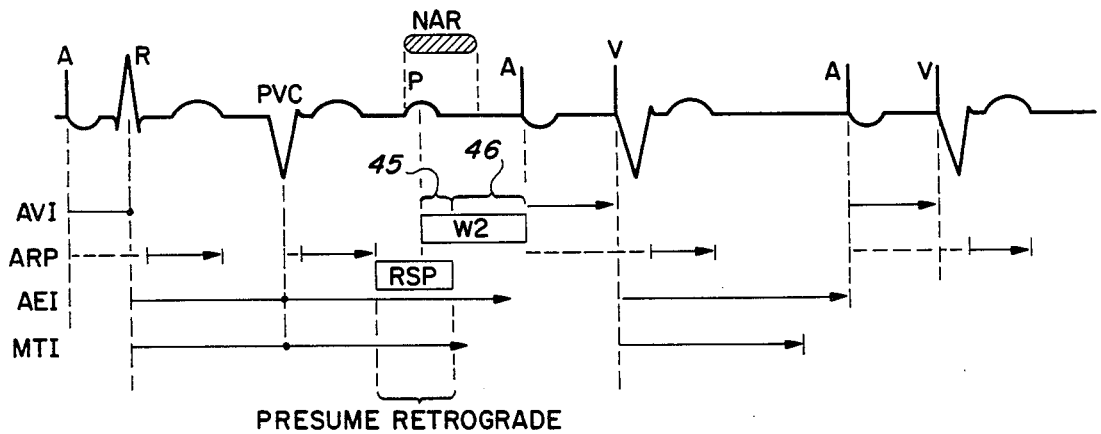

FIGS. 6A, 6B, and 6C illustrate alternative responses to a PVC in accordance with the teachings of the present invention in order to avoid the triggering of a PMT. First, with reference to a first embodiment shown in FIG. 6A, conventional PVC detection circuitry is used in order to signal the occurrence of a PVC. In response to the detection of a PVC, the atrial refractory period is extended for the purpose of blocking out any atrial activity that may occur during this time. At the conclusion of the extended atrial refractory period, a prescribed alert period, designated in FIG. 6A as W1, is initiated. An atrial stimulation pulse, or A-pulse, is not applied by the pacemaker until this atrial alert period W1 times out. The duration of this alert period W1 assures that the atrial stimulus will always be effective, even if a sinus P-wave occurs near the end of the refractory period, as shown in FIG. 6A. Values for the alert period W1 may be from 100 to 450 msec, preferably 300-350 msec. The effect of this response is that one beat of the heart will in fact be at a slower rate or longer interval. However, as indicated previously, this is quite satisfactory for one beat, and avoids the problem of potentially inducing a PMT. If a sinus P-wave occurs during the alert period, that is, during W1, then such sensing inhibits the generation of a subsequent A-pulse and the start of the A-V interval is initiated from the sensed sinus P-wave.

In the second embodiment shown in FIGS. 6B and 6C, a refractory sense period, RSP, is added to the end of the atrial refractory period, ARP. Atrial activity occurring during the RSP is sensed. However, such sensing is presumed to be a retrograde event, not a sinus event. In response to sensing such a retrograde event (FIG. 6B), an alert time window W2 is immediately initiated. This time window or period W2 is divided into a refractory portion 45 and an alert portion 46. In a preferred configuration, W2 is 350 msec, with a 100 msec refractory portion and a 250 msec alert portion. An A-pulse is generated at the conclusion of the W2 time period (as shown in FIG. 6B), unless a natural or sinus P-wave is previously sensed during the alert portion 46 of W2 (not shown in FIG. 6B). Either the generating of an A-pulse at the conclusion of W2 or the sensing of a P-wave during the alert portion 46 of W2 initiates the A-V interval as described previously. If no retrograde activity is sensed during the refractory sense period RSP, as shown in FIG. 6C, then the kinterval W2 is not inserted into the pacing interval, and the operation of the pacemaker is thereafter controlled in normal fashion (an A-pulse is generated at the conclusion of the atrial escape interval, unless a natural P-wave is sensed prior to the timing out of AEI).

In a third embodiment of the invention shown in FIG. 6D, any atrial activity sensed after a PVC and the atrial refractory period ARP, is presumed to be a valid P-wave. In accordance with this third embodiment, the post PVC sensing of atrial activity suspends the maximum tracking interval, MTI, and triggers the beginning of the A-V interval. At the conclusion of the A-V interval, a ventricular pulse is provided (unless, of course, an R-wave is sensed prior to the termination of the A-V interval, as in conventional demand-type pacing). This action causes the heart to be paced at a "fast rate" that exceeds the maximum pacing rate, as set by the combined MTI+AVI intervals. Such a "fast rate" is not physiologically damaging to the patient providing it does not continue over a prolonged period of time. Accordingly, as is evident to those skilled in the art, counting circuitry or equivalent can be used to prevent the pacer from maintaining this "fast rate" for more than a prescribed number of cardiac cycles, such as four (4). After this prescribed number of cardiac cycles, the pacemaker reverts to a backup mode, such as VVI, for at least one cycle.

If, in the third embodiment, no atrial activity is sensed after a PVC and the ARP, then the pacer provides an atrial pulse at the conclusion of the AEI in conventional manner.

It is noted that for the first embodiment previously described, once a PVC is detected the normal AEI and MTI intervals are aborted. For the third embodiment, the normal MTI interval is aborted or suspended after sensing a PVC.

A fourth embodiment of the present invention that could be used as a variation of any of the previously described embodiments is to shorten the A-V interval so as to make the V-pulse occur a little sooner in the cardiac cycle following a PVC, thereby further avoiding or preventing long V-to-V intervals, which long V-to-V intervals enhance the likelihood of additional premature ventricular contractions. It is also noted that shortening the A-V interval further reduces the likelihood of retrograde conduction.

As indicated previously, there exists other mechanisms in addition to the occurrence of a PVC that could possibly trigger a PMT. Accordingly, in accordance with the teachings of the present invention, a procedure or process is provided for terminating a PMT once a PMT is initiated. Simply stated, this PMT terminating process comprises applying one of the above-described PVC responses—e.g., inserting the alert window W1 in accordance with the teachings of FIG. 6A, or inserting the RSP period and possibly the window W2 in accordance with the teachings of FIGS. 6B and 6C, or suspending the MTI in accordance with the teachings of FIG. 6D—after n PMT cycles, and continuing to apply the PVC response at the conclusion of every m PMT cycles until the PMT is broken, where n and m are prescribed numbers. For example, in accordance with one embodiment of this PMT terminating process, ten cycles of a PMT would be counted, at which point one of the above-described PVC responses would be applied to the pacing cycle. This PVC response would be reapplied or reinserted into the pacing cycle every 128 PMT thereafter, until the PMT was broken.

Figure 7:
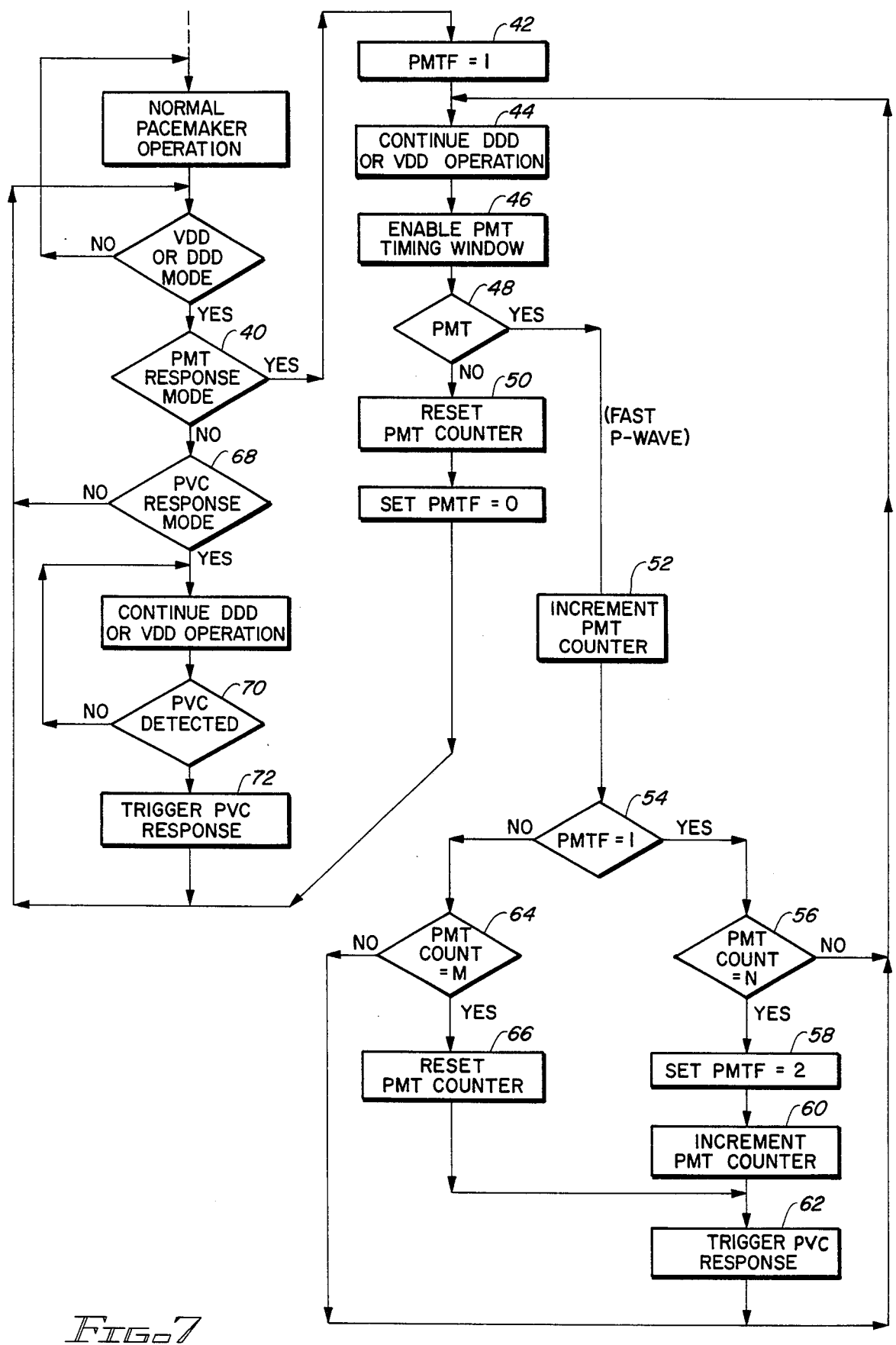
FIG. 7 is a flow diagram showing the basic PMT terminating process of the present invention.

This PMT terminating process is illustrated in the functional flow diagram of FIG. 7. In FIG. 7, it is assumed that an atrial tracking dual-chamber, pacemaker is operating in either the DDD or VDD mode of operation. If this is the case, and assuming that a PMT response mode has been enabled, as indicated at decision block 40 in FIG. 7, then an appropriate PMT flag is set. This is illustrated at block 42 where the flag identified as PMTF is set equal to 1. Once this flag, or equivalent, is set, the normal VDD or DDD operation of the pacemaker continues, as indicated at block 44. At the beginning of each pacing interval, however, a PMT timing window is initiated as indicated at block 46. As will be explained in more detail below, this PMT timing window allows a determination to be made, at decision block 48, as to whether a PMT condition exists. This decision is typically made by determining whether the P-wave occurring in the cardiac cycle is a "fast" P-wave or a "slow" P-wave. A "fast" P-wave is one that occurs in a PMT cycle, whereas a "slow" P-wave is any other P-wave. If a determination is made that a "slow" P-wave has occurred, then that is indicative of the breaking of the PMT. Other events, not shown in FIG. 7, in addition to the detection of a "slow" P-wave, also operate to indicate the breaking of the PMT, such as the occurrence of an R-wave. Accordingly, if no PMT condition exists a PMT counter is reset, as indicated at block 50. If, however, the determination is made that the P-wave is a "fast" P-wave, then the PMT counter is incremented, as shown at block 52.

After the PMT counter is incremented, a determination is made at decision block 54 as to which phase of the PMT terminating process is currently being carried out. The first phase is prior to the triggering of the first PVC response after a prescribed count of n PMT cycles. The second phase is the reinsertion of the PVC response after the occurrence of a prescribed count of m additional PMT cycles. For purposes of the flow diagram shown in FIG. 7, the particular phase of the PMT terminating process is monitored by the value of the fla PMTF. Hence, when PMTF has a value of one, that indicates that the first phase of the PMT terminating algorithm or process is currently in operation. If such is the case, then a decision is made at decision block 56 as to whether the PMT count, as held or otherwise determined in the PMT counter, has reached the value of n. If not, then the next pacing cycle is allowed to continue, during which another determination is made as to whether a "fast" or "slow" P-wave is present or if the PMT has otherwise been terminated. If fast P-waves sequentially occur, indicating that a PMT is in fact occurring, each cycle of the PMT increments the PMT counter an additional count until the PMT count reaches the value of n. When this occurs, then the flag PMTF is set equal to 2 at block 58, indicating that the second phase of the PMT terminating process is about to begin. In this second phase, the PMT counter is again incremented, as indicated at block 60, and the desired PVC response is triggered, as indicated at block 62. As previously described, this PVC response may be any of the responses shown in FIGS. 6A-6D, or variations thereof. These responses disrupt the rhythm of the PMT cycle and prevent the conditions that allow the PMT to continue. If, for whatever reason, the PMT continues, and "fast" P-waves are still sensed, then the second phase of the PMT terminating process continues. In this second phase, a decision is made at the decision block 64 as to whether the PMT counter has reached a count of m PMT cycles. If the count is less than m cycles, then the next pacing cycle continues during which another determination is made as to whether a "fast" or "slow" P-wave is present. If the count has reached m cycles, the PMT counter is reset, at block 66, and the PVC response is again triggered, at block 62. If "fast" P-waves continue in each cycle, the PMT counter will be incremented each cycle as before at block 52. In this fashion, after every m PMT cycles, the PVC response will be re-triggered.

As previously indicated, in one embodiment of the PMT terminating process of the present invention, the count n is programmed to a value of 10, and the count m is programmed to a value of 128. In an alternative embodiment of the invention, the count n is programmed to a value of 127, and the count m is programmed to a value of 128. Other values of n and m could, of course, be selected as dictated by the particular needs of the patient. It is significant to note that this terminating process does not involve the dropping of any ventricular stimuli, as has been done in the prior art.

Still referring to FIG. 7, if, at decision block 40, it is determined that the PMT response mode is not enabled, then a decision can still be made as to whether the PVC mode is enabled, as indicated at decision block 68. If so, then the normal operation of the VDD or DDD pacer continues with the PVC detect logic enabled. Enabling of the PVC detect logic causes a decision to be made with respect to every sensed ventricular activity to determine whether such activity was a PVC, as indicated at decision block 70. If a PVC is detected, then an appropriate PVC response is triggered, as indicated at block 72, and as previously described in connection with FIGS. 6A, 6B-6C, or 6D.

As those skilled in the art will recognize, numerous variations and modifications of the functional flow diagram shown in FIG. 7 are possible to achieve the same desired result. For example, it would be possible to enable the PMT response mode and the PVC response mode automatically whenever the VDD or DDD mode of the pacer is selected. In such an instance, a determination would be made every cardiac cycle as to whether the ventricular activity was a PVC, and as to whether the atrial activity represented a "fast" or "slow" P-wave. Further, it is noted that many modern implanted pacemakers employ microprocessors as the pulse generation control logic. Hence, by loading an appropriate program, or software, into the pacemaker's memory, the desired results illustrated in connection with FIGS. 6A-6D and/or FIG. 7 can be achieved under control of the microprocessor.

In the description of FIGS. 8–13 that follows, it is noted that the circuitry described in primarily directed to the circuitry used with the first embodiment of the PVC response previously described in connection with FIG. 6A. This circuitry is also suited for use with the other embodiments of the invention described in connection with FIGS. 6B—6D, and FIG. 7. Adaptation of the circuitry for a desired embodiment can be readily accomplished by those skilled in the art given the description presented herein.

Figure 8:
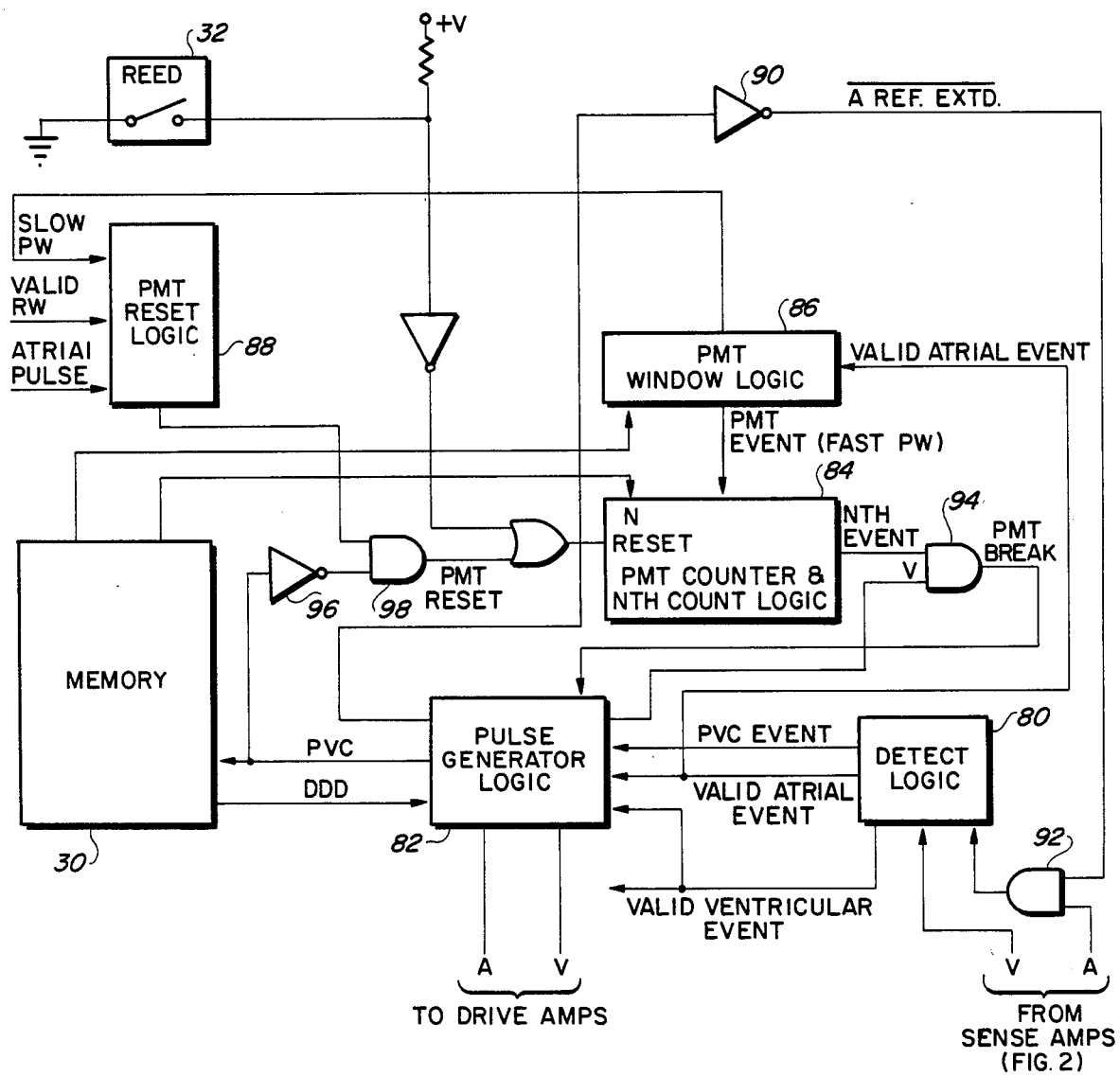
FIG. 8 is a block diagram of the PVC response and PMT terminating circuits of the present invention, and indicates the relationship of these circuits to the overall pacemaker block diagram of FIG. 2.

In FIG. 8, a block diagram of the circuitry used to realize the operation of the present invention is shown. It is noted that with the exception of the reed switch 32 and the memory circuitry 30, all of the blocks shown in FIG. 8 comprise a portion of the Pulse Generator and Control Logic 12 of FIG. 2. As seen in FIG. 8, this circuitry includes detection logic 80, pulse generator logic 82, PMT counter and Nth count logic 84, PMT window logic 86, and PMT reset logic 88. The detection logic 80 is coupled to the sense amplifiers 18 and 20 of FIG. 2. For purposes of the present invention, the primary function of the detection logic is to detect the occurrence of a PVC event. In accordance with the first embodiment described above, upon detecting a PVC event, the pulse generator logic 82 generates an AREF EXTD signal that is used to extend the atrial refractory period. The inverse of this signal, inverted by gate 90, is compared at gate 92 with activity sensed by the atrial sense amplifier 18. Any atrial activity that occurs subsequent to the atrial refractory period is applied ot the PMT window logic 86. It is the primary function of the PMT window logic to determine whether the sensed atrial activity is a "fast" P-wave, indicating the presence of a PMT, or a "slow" P-wave, indicating a non-PMT situation. If the sensed atrial activity is determined to be a "fast" P-wave, this is defined as a "PMT event" that is used to clock the PMT counter and Nth count logic 84. After the PMT counter 84 has been clocked a prescribed number of times, a PMT terminal count, or nth event signal, is generated and synchronized with a V-pulse at gate 94. The output of gate 94 is a PMT break signal that is directed back to the pulse generator logic 82 in order to trigger the "PVC response" intended to break the PMT.

If the PMT window logic 86 determines that the sensed atrial activity is a "slow" P-wave, or if other specified events occur, then the PMT reset logic 88 generates the appropriate signals needed to reset the PMT counter 84. As indicated in FIG. 8, other events which could also reset the PMT counter 84 include generation of an A-pulse or the sensing of a naturally-occurring R-wave.

As noted in FIG. 8, the pulse generator logic 82 genearates a PVC response state signal directed to memory 30 and to an inverter gate 96. Memory 30 controls the value of n and the size or length of the PMT window generated by the PMT window logic 30 so as to change the values of AEI and ARI appropriately. Inverter gate 96 directs the inverse of the PVC response signal to an AND gate 98, the other input of which is received from the PMT reset logic 88. With this arrangement, the PMT reset logic 88 can not direct a PMT reset signal to the PMT counter 84 until the next succeeding cycle from the cycle in which the PVC event was detected. This prevents the PMT counter from possibly being reset during the PMT response. Thus, the PMT counter is not reset until the next cycle, thereby providing an opportunity to verify that the PMT cycle has in fact been broken.

It is to be understood that the block diagram of FIG. 8, and the above description thereof, is primarily functional, and that the actual functions described could be carried out by those skilled in the art in numerous ways. Further, some functions related to the overall operation of the pacemaker, not particularly relevant to an understanding of the operating principles of the present invention, have not been included in FIG. 8.

Figure 10:
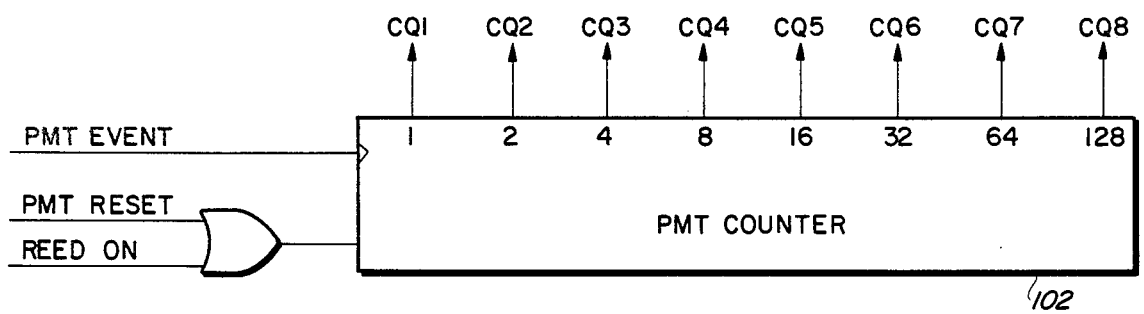
FIG. 10 is a logic diagram of the PMT Counter of FIG. 8 for a specific embodiment of the invention.

Referring next to FIGS. 9 and 10, a logic diagram of the PMT counter and Nth count logic 84 is illustrated. The embodiment shown in FIG. 9 is for a particular embodiment wherein a PMT terminal count signal, identified as PMT TCN in the figures, is generated during the nth PMT cycle and the mth PMT cycle. (When PMT3=0, n=10 and m=128; when PMT3=1, n=127 and m=128.) A PMT counter 102 (FIG. 10) is realized using a conventional multi-stage counter realized with appropriate logic circuitry. This counter generates the signals CQ1–CQ8 as a function of the count held therein. The counter 102 is clocked by the PMT EVENT line originating with the PMT window logic 86 (FIG. 8). The counter signals CQ1–CQ8 are logically combined as illustrated in FIG. 9 in order to generate the PMT TCN signal at the occurrence of the Nth event. The signal PMT 3 shown in FIG. 9 is a select signal used to select either the 10th count or the 127th count as the Nth event, the occurrence of which is indicated by the PMT TCN signal.

Referring to FIG. 11, a simplified logic diagram of the circuitry used to generate the atrial refractory extended signal, AREF EXTD, is shown. A fixed time interval, identified as T1, is used to define the extended signal (see timing diagrams of FIGS. 14 and 16). This T1 signal is applied to inverter gates 105 and 106. The output of gate 105 is further applied to a 3-input AND gate 108. A PVC response signal, generated in response to the sensing of a PVC event or other prescribed activity, (which signal is described more fully below in connection with the description of FIG. 12), is applied to another input of the AND gate 108, and to the input of another 2-input AND gate 110. The other input to the gate 110 is the output of the inverted gate 106. The output of the AND gate 110, is the AREF EXTD signal and, is thus the equivalent of the fixed time interval T1 enabled only when the PVC response signal is present. Similarly, the output of the gate 108, identified as "Set Alert Period", is the time interval T1 enabled only during the PVC state and further enabled only if the VDD or DDD mode is selected. The generation of this signal forces the V-A interval, or AEI, to be extended by a prescribed value T1, as described more fully below in conjunction with the logic timing diagrams of FIG. 14.

FIG. 12 shows a simplified logic diagram of the PVC detection logic 80 of FIG. 8. In FIG. 12, the signal IRW refers to an inhibit R-wave signal, which signal is generated whenever a valid ventricular electrical activity is sensed. The signal LIPW refers to a latched IPW signal and is generated by any P-wave that falls within the maximum track interval (MTI). The signal AEI is the atrial escape interval. The signal $P_{noise}$ is a signal that is present when atrial channel noise has been detected. The inverse of the IRW and AEI signals, and the LIPW, and $P_{noise}$ signals are applied ot the inputs of NOR gate 112. The output of NOR gate 112 will thus only assume a high logic value when all of the input signals supplied thereto are at a low logic value (signals not present). The only time during which an IRW and AEI signal would be present in combination with the absence of the other named signals would be during the occurrence of a PVC. Hence, the output of NOR gate 112 goes high upon the occurrence of a PVC event. If the proper pacer mode is selected—that is, the VDD or DDD mode—then this signal is passed through AND gate 114 and OR gate 116 to the D input of flip flop 118, which flip flop 118 is clocked by an appropriate clock signal so as to generate a PVC response signal at the Q output thereof. The PMT terminal count signal, PMT TCN, in combination with the generation of a V-pulse, applied through gate 94 and OR gate 116, can also set the flip flop 118 to the PVC state. Such a condition occurs when it is desired to trigger the PVC response in accordance with the PMT terminating process described in conjunction with FIG. 7.

Still referring to FIG. 12, the PVC state flip flop 118 is reset by the occurrence of a valid atrial event. The atrial alert period (identified as W1 in FIG. 6A, and W2 in FIG. 6B), is generated by combining the PVC state signal with an AALERT signal at gate 120. The AALERT signal may be any desired programmed value, and typically will have the value from 300–350 msec. For the second embodiment described in connection with FIG. 6B, W2 is preferably 350 msec, and is divided into a 100 msec refractory portion and a 250 msec alert portion.

Referring next to FIG. 13, a simplified logic diagram of the PMT window logic 86 and PMT reset logic 88 of FIG. 8 is illustrated. The signals PMT 1 and PMT 2 are control signals used ot select one of three possible time windows. The signals T1 and T2 are fixed time intervals, with preferred values of 489 and 413 msec, respectively. It is to be emphasized that while these values of T1 and T2 are preferred, any appropriate value could be used. As previously indicated in connection with FIG. 12, the signal LIPW represents any P-wave falling within the maximum tracking interval. The signal PW represents any other P-wave. The function of the logic circuitry shown in FIG. 13 is to determine whether any given atrial activity is the result of a "slow" P-wave or a "fast" P-wave. If a "fast" P-wave is detected, then a PMT CLK signal is generated in order to increment the PMT counter. If, however, a "slow" P-wave is detected then a PMT reset signal is generated. The circuitry shown in FIG. 13 is representative of one of a plurality of ways in which this function could be realized.

The operation of the logic circuitry shown in FIGS. 9–13 can be better understood with reference to the logic timing diagrams of FIGS. 14–16. FIG. 14 describes the first embodiment PVC response described previously in connection with FIG. 6A. In FIG. 14, a response to the detection of a PVC is indicated. The top two lines of FIG. 14 represent the A-pulse and V-pulse stimulation signals, respectively, that are generated by the pulse generator logic 82. The third and fourth lines of FIG. 14 represent the outputs from the sense amplifiers 18 and 20, respectively, of FIG. 2. The fifth line of FIG. 14 is the atrial refractory period that is generated in conventional manner by the operation of the pacemaker. The sixth line of FIG. 14 illustrates the extended atrial refractory period generated by the circuitry of FIG. 11 in response to the detection a PVC event (see line 4). Line 7 of FIG. 14 illustrates the ventricular refractory period. Note that all of the refractory periods are initiated by the occurrence of a V-pulse or the occurrence of sensed ventricular activity. Line 8 of FIG. 14 illustrates the atrial escape interval, or AEI, sometimes referred to as the V-A interval or V-A delay. the first occurrence of this interval is at a programmed interval. The second occurrence of this interval is reset at the occurrence of the PVC event and forced to a fixed interval T1. Line 9 of FIG. 14 illustrates the P Alert time period, that is, the time during which electrical activity can be sensed in the atrium. During the first occurrence, this interval represents the difference between the atrial refractory period (line 5) and the atrial escape interval (line 8). During the second occurrence, this period does not begin until the end of the extended atrial refractory period (line 6), and then it assumes a preselected value (W1) of from 300–350 msec. The PVC response signal (line 10) is set at the occurrence of the PVC EVENT and is reset at the termination of the P Alert signal (line 9). This signal line is disabled during the A-V delay.

FIG. 15 shows a logic timing diagram associated with the second alternative embodiment of the PVC response of the present invention, previously described in conjunction with FIGS. 6B and 6C. In FIG. 15 lines 1–5, and 7–10 correspond to the same signals as described in connection with FIG. 14. However, in FIG. 15, it is noted that the atrial refractory period is not extended as was done in conjunction with the embodiment of FIG. 14. Rather, on line 6A in FIG. 15, a retrograde sense window (of a programmable value, $T_A$) is triggered whenever the PVC state is enabled (line 10) and at the conclusion of the atrial refractory period (line 5). If retrograde activity is sensed during this retrograde window, as indicated by the solid lines in FIG. 15, then a secondary atrial refractory period is initiated as shown on line 6B. In the preferred embodiment, this secondary refractory period assumes a value of 100 msec, and represents an absolute refractory time interval. At the conclusion of this secondary atrial refractory period, the P alert period (line 9) is initiated and has a duration of a prescribed value (250 msec in the preferred embodiment). The 100 msec secondary atrial refractory period and the 250 msec P alert period thus comprise the W2 time period referred to in conjunction with FIG. 6B. The dashed lines in FIG. 15 on lines 1, 6A, 6B, 8, 9, and 10 represent the waveform response when no retrograde activity is sensed during the retrograde window.

Referring next to FIG. 16, a logic timing diagram illustrates the operation of the PMT terminating process of the present invention. Lines 1–10 of FIG. 16 correspond to the same signals as are shown on lines 1–10 of FIG. 14. However, the horizontal time scale of FIG. 16 covers a much longer time period than is shown in FIGS. 14 or 15 in order to illustrate how the PMT counter 84 (FIG. 8) is incremented and reset. It is assumed in FIG. 16 that the pacer mediated tachycardia condition is present and that the circuitry has been counting and tracking retrograde conduction ("fast" P-waves) for several cycles. As indicated on line 12, the PMT clock signal is derived from the sensing of fast P-waves (line 3). It is assumed that the first occurrence of a fast P-wave in FIG. 16 corresponds to incrementing the PMT count (line 14) to the count of 9. The next occurrence of a fast P-wave, which is responsible for generating the second PMT clock pulse (line 12), causes the PMT counter to increment to the counter 10. In one embodiment, it is at this count at which the PMT counter generates the terminal count signal, PMT TCN, as indicated on line 11. The effect of the PMT TCN signal is to trigger a PVC response as previously described. This PVC response is synchronized with the occurrence of the next V-pulse (line 2). Hence, coincident with the generation of this next V-pulse, the atrial refractory period is extended, as indicated on line 6. At the conclusion of this extended atrial refractory period, an alert period W1 is generated. At the conclusion of this alert period W1, the next A-pulse will be generated, which A-pulse is followed, for the situation shown in FIG. 16, by a natural R-wave (line 4). The occurrence of the naturally-occurring R-wave is indicative that the PMT has been broken, and normal pacer operation continues thereafter. It is noted that the PMT counter is not reset until a determination has been made that the PMT has been broken, as indicated by the sensed R-wave (line 4). Thus, the counter is reset to zero at this time. If the PMT had not been broken, then the PMT counter would have continued to be incremented until it reached the next terminal count value (128 counts after the 10th count for the embodiment shown), at which time another PVC response would have been triggered.

It is noted that while the PMT terminating process shown in FIG. 16 uses the first embodiment of the PVC response circuitry (FIGS. 6A and 14) to terminate the PMT, this PMT terminating response could also be implemented using the second or third embodiments or variations thereof of the PVC response circuitry (FIGS. 6B–6D and 15).

In the preferred embodiment, the circuitry described in conjunction with FIG. 2, and FIGS. 8–13 is realized using primarily CMOS LSI circuitry. While many of the implementation details associated with these circuits have not been disclosed herein, those skilled in the art could readily implement the necessary circuitry given the logic timing diagrams and description of the invention provided herein. Moreover, while the invention has been described by means of specific embodiments and applications thereof, it is understood that numerous modifications and variations could be made thereto by those skilled in the art without departing from the spirit and scope of the invention. It is therefore to be understood that within the scope of the appended claims, the invention may be practiced otherwise than as specifically described herein.

We claim:

1. A method of operating a dual-chamber cardiac pacemaker, said dual-chamber cardiac pacemaker including means for sensing a premature ventricular contraction (PVC), comprising the steps of:
    (a) generating an extended atrial refractory period upon the sensing of a PVC, said extended atrial refractory period comprising a first prescribed time period during which electrical activity in the atrium of a heart being paced by said pacemaker is not sensed by said pacemaker;
    (b) generating an atrial alert time interval that is initiated at the conclusion of the extended atrial refractory period, said atrial alert time interval comprising a second prescribed time period during which electrical activity in the atrium is sensed, but during which no pacemaker-generated stimulation pulses are delivered to the atrium;
    (c) delivering a pacemaker-generated stimulation pulse to the atrium at the conclusion of the atrial alert time interval only when no electrical activity is sensed in the atrium during the atrial alert time interval; and
    (d) generating an A-V time interval that is initiated at the conclusion of the atrial alert time interval, said A-V time interval comprising a third time period at the conclusion of which a ventricular stimulation pulse may be selectively delivered to the ventricle of the heart by said pacemaker.

2. The method of claim 1 wherein the ventricular stimuation pulse is delivered to the ventricle at the conclusion of the A-V time interval in step (d) only when there is no sensed electrical activity in the ventricle during the immediately preceeding A-V time interval.

3. The method of claim 1 wherein the A-V time interval in step (d) is different than a normal A-V time delay period used within said pacemaker.

4. A method of operating a dual-chamber pacemaker, said dual-chamber cardiac pacemaker including means for sensing a premature ventricular contraction (PVC), comprising the steps of:
    (a) generating a first time period that begins upon the sensing of a PVC;
    (b) generating a second time period that is initiated upon the occurrence of a first prescribed event occurring within said first time period;
    (c) delivering an atrial stimulation pulse to the atrium of a heart being paced by said pacemaker at the conclusion of the second time period, unless a second prescribed event occurs during said second time period, in which case no atrial stimulation pulse is generated;
    (d) generating a third time period that is initiated at the conclusion of the second time period; and
    (e) delivering a ventricular stimulating pulse to the ventricle of the heart at the conclusion of the third time period providing a third prescribed event has previously occurred.

5. The method of claim 4 wherein the third prescribed event of step (e) comprises the absence of sensed electrical activity in the ventricle of the heart during said third time period.

6. The method of claim 4 wherein the third prescribed event of step (e) comprises the absence of sensed electrical activity in the ventricle of the heart for a prior time period that includes said third time period.

7. The method of claim 4 wherein the third time period is different than a normal A-V delay period used within said pacemaker.

8. The method of claim 4 wherein the first prescribed event of step (b) comprises the timing to of said first time period.

9. The method of claim 4 wherein the first prescribed event of step (b) comprises an atrial event.

10. The method of claim 9 wherein said atrial event comprises the sensing of electrical activity in the atrium of the heart.

11. The method of claim 4 wherein said second time period comprises an atrial alert time period that has a prescribed duration that falls within the range of from 250 to 450 msec.

12. The method of claim 11 wherein said second time period has a fixed duration selected to fall in the range of from 300 to 350 msec.

13. The method of claim 4 wherein said second time period is divided into first and second portions, the first portion of which is refractory with respect to atrial electrical activity.

14. A method of operating a dual-chamber pacemaker, said pacemaker including means for sensing atrial and ventricular activity, as well as means for sensing a premature ventricular contraction (PVC), comprising the steps of:
  (a) generating, in response to sensing, ventricular activity, an atrial escape interval and a maximum tracking interval, at least a latter portion of said atrial escape interval comprising a time period during which atrial activity is sensed, an A-V interval being generated at the earliest occurrence of either: (1) the sensing of atrial activity within the latter portion of said atrial escape interval or (2) the conclusion of said actual escape interval, said maximum tracking interval plus said A-V interval comprising a time period that defines a maximum pacing rate of said pacemaker;
  (b) suspending said atrial escape interval and said maximum tracking interval in response to the sensing of atrial activity within the latter portion of said atrial escape interval that occurs subsequent to the sensing of a PVC;
  (c) generating, in response to the sensing of atrial activity, said A-V interval; and
  (d) generating a ventricular stimulating pulse at the conclusion of said A-V interval.

15. The method of claim 14 wherein the suspension of the atrial escape interval and the maximum tracking interval in response to the sensing of post PVC atrial activity in accordance with step (b) is continued only for a prescribed number of consecutive cardiac cycles.

16. A method of breaking a pacer mediated tachycardia (PMT) in a dual-chamber cardiac pacemaker, said dual-chamber cardiac pacemaker including sensing means for selectively sensing electrical activity in a ventricle and an atrium of a heart, and pacing means for selectively delivering stimulation pulses to at least the ventricle in accordance with a prescribed timing sequence, said method of breaking a PMT comprising the steps of:
  (a) counting a prescribed number of PMT cycles; and
  (b) extending the time at which said pacing means delivers one of said stimulation pulses to the ventricle in the next PMT cycle, thereby changing the V—V interval of this next PMT cycle.

17. The PMT breaking method of claim 16 further including the step of:
  (c) repeating steps (a) and (b) until the PMT is broken.

18. The PMT breaking method of claim 17 wherein the prescribed number of PMT cycles counted in step (a) includes a first prescribed number of PMT cycles to be counted prior to the extension of the initial V—V interval applied in step (b), and a second prescribed number of PMT cycles to be counted subsequent to the initial V—V interval extension.

19. The PMT breaking method of claim 18 wherein the first prescribed number of PMT cycles to be counted is at least 10.

20. The PMT breaking method of claim 19 wherein the second prescribed number of PMT cycles to be counted is no more than 130.

21. The PMT breaking method of claim 18 wherein the first prescribed number of PMT cycles to be counted is at least 127.

22. The PMT breaking method of claim 16 wherein step (b) comprises
  (1) applying an extended atrial refractory period to the sensing means of said pacemaker immediately subsequent to the generation of the ventricular stimulation pulse of the selected PMT cycle, said extended atrial refractory period comprising a time interval during which the sensing means is unable to sense electrical activity in the atrium,
  (2) applying an atrial alert period to the sensing means and pacing means of the pacemaker immediately subsequent to the timing out of said extended atrial refractory period, said atrial alert period comprising a time interval during which the sensing means is able to sense electrical activity in the atrium, but during which the pacing means is inhibited from delivering any stimulation pulses to the atrium, and
  (3) applying an A-V interval period to the sensing means and pacing means of the pacemaker immediately subsequent to the timing out of said atrial alert period, said A-V interval comprising a time interval after the duration of which a ventricular stimulation pulse will be delivered to the ventricle unless electrical activity is sensed in the ventricle during said A-V interval.

23. The PMT breaking method of claim 22 wherein said A-V interval period comprises a selected time period that is different than a normal A-V delay time period used within said pacemaker.

24. The PMT breaking method of claim 16 wherein step (b) comprises
  (1) applying a first time interval to the sensing means of said pacemaker immediately subsequent to the generation of the ventricular stimulation pulse of the selected PMT cycle, said first time interval comprising a refractory period during which the sensing means is blocked from sensing electrical activity in the atrium,
  (2) applying a second time interval to the sensing means of the pacemaker immediately subsequent to the timing out of the first time interval, said second time interval comprising a time during which the sensing means is able to sense electrical activity in the atrium,
  (3) if atrial electrical activity if sensed during said second time interval, applying a third time interval to the sensing means of the pacemaker immediately subsequent to the sensing of said atrial electrical activity during said second time interval,
  (4) applying a fourth time interval to the sensing and pacing means of the pacemaker immediately subsequent to the ending of said third time interval of step (3), or if no atrial electrical activity is sensed during said second time interval, applying said fourth time interval immediately subsequent to an atrial escape interval, said atrial escape interval being initiated concurrent with said first time period and
  (5) delivering a ventricular stimulation pulse to the ventricle at the conclusion of said forth time interval in the absence of sensed ventricular activity occurring during said fourth time interval.

25. In a pacemaker having means for detecting the occurrence of a premature ventricular contraction (PVC), and means for sensing first and second cardiac events associated with the operation of said pacemaker, a system for responding to a PVC comprising:
  means for generating a first time period that begins upon the sensing of a PVC by said PVC detection means;
  means for generating a second time period that is initiated upon the occurrence of said first prescribed cardiac event occurring during said first period;

means for generating a third time period that is initiated upon the occurrence of said second prescribed cardiac event; and delivery means for selectively delivering a stimulation pulse to a ventricle of a heart being paced by said pacemaker at the end of said third time period.

26. The pacemaker of claim 25 wherein the first prescribed event that triggers the generation of said second time period is the timing out of said first time period.

27. The pacemaker of claim 26 wherein said pacemaker further includes means for sensing atrial activity in an atrium of the heart, and wherein said delivery means further delivers a stimulation pulse to the atrium at the end of said second time period unless atrial activity is sensed in said atrium during said second time period.

28. The pacemaker of claim 27 wherein the second prescribed event that triggers the generation of said third time period is the sensing of atrial activity during said second time period.

29. The pacemaker of claim 27 wherein the second prescribed event that triggers the generation of said third time period is the timing to of said second time period.

30. The pacemaker of claim 25 wherein said pacemaker further includes means for sensing atrial activity in an atrium of the heart, during a latter portion of said first time period, and wherein the first prescribed event that triggers the generation of said second time period comprises the sensing of atrial activity in the atrium by said atrial sensing means.

31. The pacemaker of claim 30 wherein said second time period is divided into an initial refractory portion and a subsequent alert portion, said atrial sensing means being inoperable during said refractory portion and operable during said alert portion.

32. The pacemaker of claim 25 wherein said third time period comprises a time period that is different than an A-V delay period used by said pacemaker when a PVC is not sensed.

33. A cardiac pacemaker including atrail and ventricular sensing means for respectively sensing atrial and ventricular depolarizations of a heart;

pulse generating means for generating stimulation pulses that may be selectively delivered to the ventricle in response to a ventricular trigger signal;

timing means for generating said ventricular trigger signal in response to a prescribed timing sequence, said timing means including inhibiting means responsive to said ventricular sensing means for inhibiting said ventricular trigger signal in response to sensed ventricular depolarizations, premature ventricular contraction (PVC) means for sensing a premature ventricular contraction, said premature ventricular contraction comprising a ventricular depolarization that occurs subsequent to a prior ventricular depolarization and prior to an atrial depolarization or the timing out of an atrial escape interval, whichever occurs first, and for generating a PVC signal in response to the sensing of a PVC, means for generating an extended atrial refractory period in response to said PVC signal, said extended atrial refractory period comprising a period of time during which the atrial sensing means of said pacemaker is not operable, means for generating an atrial alert time window subsequent to the timing to of said extended atrial refractory period, said atrial alert time window comprising a prescribed period of time during which the atrial sensing means is operable, and means for generating an A-V interval that begins at the conclusion of said atrial alert time window, said A-V interval comprising a prescribed period of time during which the ventricular sensing means is operable, said ventricular trigger signal being generated at the conclusion of said A-V interval unless said ventricular trigger signal is inhibited by said inhibiting means.

34. The pacemaker of claim 33 wherein the prescribed period of time of said atrial alert time window comprises 300 to 350 msec.

35. The pacemaker of claim 33 wherein the prescribed time period of said A-V interval is shortened in response to said PVC signal.

36. The pacemaker of claim 33 further including pacemaker mediated tachycardia (PMT) breaking means within said timing means for breaking a tachycardia caused at least in part by said pacemaker, said PMT breaking means comprising tachycardia signaling means for signaling the occurrence of a sustained PMT as sensed through said atrial and ventricular sensing means, counting means responsive to said tachycardia signaling means for counting the number of cycles that occur in said sustained PMT, means for generating said PVC signal in response to a prescribed count reached by said counting means, which PVC signal triggers the generation of said extended atrial refractory period, which in turn causes said atrial alert time window and A-V interval to be generated, thereby effectuating a change in the rhythm of said sustained PMT, which change in rhythm is intended to break said PMT.

37. The pacemaker of claim 36 wherein the prescribed count reached by said counting means at which the PVC signal is generated comprises at least 10.

38. The pacemaker of claim 36 wherein the prescribed count reached by said counting means at which the PVC signal is generated comprises a count less than 150 and greater than 10.

39. The pacemaker of claim 36 wherein said PVC signal is generated at the nth count of said counting means, and every mth count thereafter until said PMT is broken, where m and n are selected integers.

40. A cardiac pacemaker including atrial and ventricular sensing means for respectively sensing atrial and ventricular depolarizations of a heart;

pulse generating means for generating stimulation pulses that may be selectively delivered to the ventricle in response to a ventricular trigger signal;

timing means for generating said ventricular trigger signal in response to a prescribed timing sequence, said timing means including inhibiting means responsive to said ventricular sensing means for inhibiting said ventricular trigger signal in response to sensed ventricular depolarizations, premature ventricular contraction (PVC) means for sensing a premature ventricular depolarization contraction, said premature ventricular contraction comprising a ventricular depolarization that occurs subsequent to a prior ventricular depolarization and prior to an atrial depolarization or the timing out of an atrial escape interval, whichever occurs first, and for generating a PVC signal in response to the sensing of a PVC, means for generating and atrial refractory period in response to said PVC signal, said atrial refractory period comprising a prescribed period of time during which the atrial sensing means of said pacemaker is not operable, means for generating a retrograde sense period subsequent to said atrial refractory period during which the atrial sensing means is operable, means for generating an atrial escape interval that begins in response to said PVC signal, said atrial escape interval comprising an AEI time period that is at least as long as the duration of the atrial refractory period followed by the retrograde sense period, means for generating an atrial alert time window of a first prescribed time period that beings in response to the sensing of an atrial depolarization occurring during the retrograde sense period, and means for generating an A-V interval that begins at the conclusion of said AEI time if no atrial depolarization is sensed during the retrograde sense period, or at the earliest occurrence of either the conclusion of said atrial alert time window or the sensing of an atrial depolarization by said atrial sensing means during said atrial alert time window, said A-V interval comprising a second prescribed time period during which the ventricular sensing means is operable, said ventricular trigger signal being generated at the conclusion of said A-V interval unless said ventricular trigger signal is inhibited by said inhibiting means.

41. The pacemaker of claim 40 wherein the first prescribed period of time of said atrial alert time window comprises 300 to 350 msec.

42. The pacemaker of claim 40 wherein the second prescribed time period of said A-V interval is shortened in response to said PVC signal.

43. The pacemaker of claim 40 further including pacemaker mediated tachycardia (PMT) breaking means within said timing means for breaking a tachycardia caused at least in part by said pacemaker, said PMT breaking means comprising tachycardia signaling means for signaling the occurrence of a sustained PMT as sensed through said atrial and ventricular sensing means, counting means responsive to said tachycardia signaling means for counting the number of cycles that occur in said sustained PMT, means for generating said PVC signal in response to a prescribed count reached by said counting means, which PVC signal triggers the generation of said atrial refractory period, followed by said retrograde sense period and, if atrial activity is sensed, said atrial alert time window, thereby effectuating a change in the rhythm of said sustained PMT, which change in rhythm is intended to break said PMT.

44. The pacemaker of claim 43 wherein the prescribed count reached by said counting means at which the PVC signal is generated comprises at least 10.

45. The pacemaker of claim 43 wherein the prescribed count reached by said counting means at which the PVC signal is generated comprises a count less than 130.

46. The pacemaker of claim 43 wherein said PVC signal is generated at the nth count of said counting means, and every mth count thereafter until said PMT is broken, where m and n are selected integers.

47. An atrial tracking dual-chamber pacemaker comprising atrial and ventricular sensing means for sensing electrical activity occurring in an atrium and ventricle of a heart, respectively;

pulse generating means coupled to said atrial and ventricular sensing means for generating a ventricular trigger signal, which ventricular trigger signal causes a ventricular stimulation pulse to be generated;

inhibiting means responsive to said ventricular sensing means for inhibiting said ventricular trigger signal whenever ventricular electrical activity is sensed within a first prescribed time period prior to the generation of said ventricular trigger signal;

timing means for controlling the operation of said atrial and ventricular sensing means in a way that minimizes the likelihood that retrograde atrial electrical activity will trigger a pacer mediated tachycardia.

48. The pacemaker of claim 47 wherein said timing means includes:

means for sensing a premature ventricular contraction (PVC); and means, responsive to the sensing of a premature ventricular contraction, for preventing the sensing of retrograde atrial electrical activity resulting from said premature ventricular contraction.

49. The pacemaker of claim 48 wherein said means for preventing the sensing of retrograde atrial electrical activity comprises:

means for generating an extended refractory time period subsequent to the sensing of the PVC;

means for sensing atrial electrical activity for an alert time period subsequent to said refractory time period; and means for generating an A-V interval subsequent to the termination of said alert time period, said ventricular trigger signal being generated by said pulse generating means at the termination of said A-V interval unless inhibited by said inhibiting means.

50. The pacemaker of claim 49 wherein said A-V interval generated by said A-V interval generating means is shortened in response to the sensing of a PVC over what it would be in the absence of sensing a PVC.

51. The pacemaker of claim 49 wherein said alert time period is terminated by the earliest occurrence of either the timing out of said alert time period or the sensing of atrial electrical activity during said alert time period.

52. The pacemaker of claim 47 wherein said timing means includes:

means for sensing a premature ventricular contraction;

means for sensing retrograde atrial activity resulting from said premature ventricular contraction; and retrograde response means for responding to the sensed retrograde atrial activity in a way that minimizes the likelihood that the retrograde atrial activity will trigger a pacer mediated tachycardia.

53. The pacemaker of claim 52 wherein said retrograde response means comprises means for generating an atrial escape interval in response to the sensing of said premature ventricular contraction, means for initiating an atrial alert period immediately subsequent to the sensing of atrial activity, if any, during said retrograde sense period;

means for generating an A-V interval subsequent to the termination of said atrial alert period, if generated, said ventricular trigger signal being generated by said pulse generating means at the termination of said A-V interval unless inhibited by said inhibiting means; and means for generating an A-V interval subsequent to the termination of said atrial escape interval when no atrial activity is sensed during said retrograde sense period.

54. The pacemaker of claim 53 wherein said atrial alert period, when generated, is terminated by the earliest occurrence of either the timing out of said alert time period or the sensing of atrial electrical activity during said alert time period.

55. The pacemaker of claim 53 wherein said atrial alert period is subdivided in an initial refractory portion and a final alert portion.

56. The pacemaker of claim 53 wherein said A-V interval assumes a first value if atrial activity is sensed during said retrograde sense period and assumes a second value, different from said first value, if atrial activity is not sensed during said retrograde sense period.

* * * * *